(12) United States Patent
Budach et al.

(10) Patent No.: US 7,064,844 B2
(45) Date of Patent: *Jun. 20, 2006

(54) SENSOR PLATFORM, APPARATUS INCORPORATING THE PLATFORM AND PROCESS USING THE PLATFORM

(75) Inventors: Wolfgang Ernst Gustav Budach, Schliengen-Mauchen (DE); Dieter Neuschaefer, Muttenz (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/994,028

(22) Filed: Nov. 8, 2004

(65) Prior Publication Data

US 2005/0117161 A1   Jun. 2, 2005

Related U.S. Application Data

(60) Continuation of application No. 10/684,071, filed on Oct. 9, 2003, now Pat. No. 6,867,869, which is a continuation of application No. 10/684,070, filed on Oct. 9, 2003, now Pat. No. 6,870,630, which is a division of application No. 10/043,629, filed on Jan. 10, 2002, now Pat. No. 6,771,376, which is a continuation-in-part of application No. 09/609,846, filed on Jul. 5, 2000, now Pat. No. 6,707,561.

(30) Foreign Application Priority Data

Jul. 5, 1999   (GB) ................... 9915703.4
May 11, 2000   (GB) ................... 0011420.7

(51) Int. Cl.
*G01B 9/02* (2006.01)
*G01N 21/64* (2006.01)
*G01N 21/66* (2006.01)

(52) U.S. Cl. .................... 356/521; 356/491; 422/82.08

(58) Field of Classification Search ................ 356/521, 356/491, 517; 422/82.05, 82.08, 82.09, 82.11
See application file for complete search history.

(56) References Cited

U.S. PATENT DOCUMENTS 4,810,658 A    3/1989   Shanks et al.

(Continued)

FOREIGN PATENT DOCUMENTS

EP    0 178 083    4/1986

(Continued)

OTHER PUBLICATIONS

Adlard, et al., The American Physical Society, Physical Review Letters, vol. 79, No. 9, "Localization of One-Photon States," pp. 1585-1587, (1997).

(Continued)

*Primary Examiner*—Gregory J. Toatley, Jr.
*Assistant Examiner*—Patrick Connolly
(74) *Attorney, Agent, or Firm*—Townsend & Townsend & Crew LLP

(57) ABSTRACT

A sensor platform for use in sample analysis comprises a substrate (30) of refractive index $(n_1)$ and a thin, optically transparent layer (32) of refractive index $(n_2)$ on the substrate, $(n_2$ is greater than $(n_1)$. The platform incorporates one or multiple corrugated structures in the form of periodic grooves (31), (33), which defines one or more sensing areas each for one or more capture elements. The grooves are so profiled, dimensioned and oriented that when coherent light is incident on the platform it is diffracted into individual beams or diffraction order resulting in reduction of the transmitted beam and an abnormal high reflection of the incident light thereby creates an enhanced evanescent field at the surface of the or each sensing area. The amplitude of this field at the resonant condition is greater by an order of approximately 100 than the field of prior art platforms so that the luminescence intensity created from samples on the platform is also increased by a factor of 100. Also disclosed are an apparatus incorporating the platform and a method of using the platform. Further increases of amplitude have been detected by using light having a linear component which gives rise to TM excitation and/or irradiating the platform from the substrate side.

26 Claims, 10 Drawing Sheets

U.S. PATENT DOCUMENTS

| | | |
|---|---|---|
| 4,828,387 A | 5/1989 | Sawyers et al. |
| 4,882,288 A | 11/1989 | North et al. |
| 4,931,384 A | 6/1990 | Layton et al. |
| 4,952,056 A | 8/1990 | Tiefenthaler |
| 4,978,503 A | 12/1990 | Shanks et al. |
| 4,992,385 A | 2/1991 | Godfrey |
| 5,006,716 A | 4/1991 | Hall |
| 5,082,629 A | 1/1992 | Burgess et al. |
| 5,164,589 A | 11/1992 | Sjödin |
| 5,186,897 A | 2/1993 | Eason et al. |
| 5,192,502 A | 3/1993 | Attridge et al. |
| 5,208,111 A | 5/1993 | Decher et al. |
| 5,242,828 A | 9/1993 | Bergström et al. |
| 5,294,402 A | 3/1994 | Schrepp et al. |
| 5,312,729 A | 5/1994 | Allen et al. |
| 5,374,563 A | 12/1994 | Maule |
| 5,415,842 A | 5/1995 | Maule |
| 5,434,663 A | 7/1995 | Maule |
| 5,436,161 A | 7/1995 | Bergström et al. |
| 5,455,178 A | 10/1995 | Fattinger |
| 5,468,620 A | 11/1995 | Molloy et al. |
| 5,478,756 A | 12/1995 | Gizeli et al. |
| 5,480,687 A | 1/1996 | Heming et al. |
| 5,491,556 A | 2/1996 | Stewart et al. |
| 5,492,840 A | 2/1996 | Malmqvist et al. |
| 5,532,170 A | 7/1996 | Buckle et al. |
| 5,554,541 A | 9/1996 | Malmqvist et al. |
| 5,631,734 A | 5/1997 | Stern et al. |
| 5,641,640 A | 6/1997 | Hanning |
| 5,663,790 A | 9/1997 | Ekström et al. |
| 5,677,196 A * | 10/1997 | Herron et al. ............... 436/518 |
| 5,712,705 A | 1/1998 | Fattinger et al. |
| 5,716,854 A | 2/1998 | Löfås et al. |
| 5,738,825 A | 4/1998 | Rudigier et al. |
| 5,770,462 A | 6/1998 | Molloy |
| 5,779,978 A | 7/1998 | Hartmann et al. |
| 5,822,472 A | 10/1998 | Danielzik et al. |
| 5,830,766 A | 11/1998 | Attridge et al. |
| 5,846,843 A | 12/1998 | Simon |
| 5,874,219 A | 2/1999 | Rava et al. |
| 5,898,503 A | 4/1999 | Keller et al. |
| 5,912,456 A | 6/1999 | Melendez et al. |
| 5,946,083 A | 8/1999 | Melendez et al. |
| 5,955,729 A | 9/1999 | Nelson et al. |
| 5,959,292 A | 9/1999 | Duveneck et al. |
| 5,965,456 A | 10/1999 | Malmqvist et al. |
| 5,972,612 A | 10/1999 | Malmqvist et al. |
| 5,981,956 A | 11/1999 | Stern |
| 6,078,705 A | 6/2000 | Neuschäfer et al. |
| 6,093,536 A | 7/2000 | Drake et al. |
| 6,111,248 A | 8/2000 | Melendez et al. |
| 6,111,652 A | 8/2000 | Melendez et al. |
| 6,127,183 A | 10/2000 | Ivarsson et al. |
| 6,141,096 A | 10/2000 | Stern et al. |
| 6,143,574 A | 11/2000 | Karlsson et al. |
| 6,183,696 B1 | 2/2001 | Elkind et al. |
| 6,191,847 B1 | 2/2001 | Melendez et al. |
| 6,198,869 B1 | 3/2001 | Kraus et al. |
| 6,200,814 B1 | 3/2001 | Malmqvist et al. |
| 6,203,989 B1 | 3/2001 | Goldberg et al. |
| 6,207,381 B1 | 3/2001 | Larsson et al. |
| 6,207,960 B1 | 3/2001 | Stern |
| 6,211,954 B1 | 4/2001 | Danielzik et al. |
| 6,218,194 B1 | 4/2001 | Lyndin et al. |
| 6,225,625 B1 | 5/2001 | Pirrung et al. |
| 6,245,578 B1 | 6/2001 | Molloy |
| 6,252,236 B1 | 6/2001 | Trulson et al. |
| 6,289,144 B1 | 9/2001 | Neuschäfer et al. |
| 6,289,286 B1 | 9/2001 | Andersson et al. |
| 6,294,327 B1 | 9/2001 | Walton et al. |
| 6,707,561 B1 * | 3/2004 | Budach et al. ............... 356/521 |
| 6,771,376 B1 * | 8/2004 | Budach et al. ............... 356/521 |
| 6,870,630 B1 * | 3/2005 | Budach et al. ............... 356/521 |
| 2002/0074513 A1 | 6/2002 | Abel et al. |
| 2003/0108291 A1 | 6/2003 | Duveneck et al. |
| 2003/0138208 A1 | 7/2003 | Pawlak et al. |
| 2003/0148542 A1 | 8/2003 | Pawlak et al. |
| 2004/0115826 A1 | 6/2004 | Budach et al. |

FOREIGN PATENT DOCUMENTS

| | | |
|---|---|---|
| EP | 0 455 067 A2 | 11/1991 |
| GB | 2 227 089 | 7/1990 |
| GB | 2 256 477 | 12/1992 |
| WO | WO 90/03382 | 4/1990 |
| WO | WO 91/16425 | 10/1991 |
| WO | WO 92/10092 | 6/1992 |
| WO | WO 95/33197 | 12/1995 |
| WO | WO 96/26432 | 8/1996 |
| WO | WO 96/35940 | 11/1996 |
| WO | WO 97/02357 | 1/1997 |
| WO | WO 97/29362 | 8/1997 |
| WO | WO 98/21571 | 5/1998 |
| WO | WO 98/27430 | 6/1998 |
| WO | WO 99/13320 | 3/1999 |
| WO | WO 99/26059 | 5/1999 |
| WO | WO 00/75644 A1 | 12/2000 |
| WO | WO 01/02839 A1 | 1/2001 |

OTHER PUBLICATIONS

Parriaux, et al., Pure Appl. Opt. 5, Printed in the UK, "Coupling gratings as waveguide functional elements," pp. 453,469 (1996).

Rosenblatt, et al., IEEE Journal of Quantum Electronics, vol. 33, No. 11, "Resonant Grating Waveguide Structures," Nov. 1997.

Dolder, et al., Derwent Abstracts, 1991-339813 [46], "Method for the Light-Induced Immobilization of Biomolecules on Chemically "inert" Surfaces" (WO 91/16425-Oct. 31, 1991).

Sychugov, et al., Sensors and Actuators, B 38-39, "Waveguide Coupling Fratings for High-Sensitivity Biochemical Sensors," pp. 360-364 (1997).

Tyagi, et al., Nature Biotechnology, "Molecular Beacons: Probes that Fluoresce Upon Hybridization," vol. 14, pp. 303-308 (Mar. 1996).

Wang, et al., Applied Optics, vol. 32, No. 14, "Theory and Application of Guided-Mode Resonance Filters," (May 10, 1993).

Kogelnik, H., "Theory of Optical Waveguides," ed. Tamit, T., Guided-Wave Optoelectronics, pp. 7-88, Springer-Verlag: New York, (1988).

* cited by examiner epifluorescence

← 5 mm → about 100 fold signal increase

ER enhancement image profile

DISC-SHAPED PLATFORM

MICROTITER / NANOTITER-TYPE
DEVICES (96/384/...)

FIG. 10

| proteo-chips incubated with | epi fluorescence | | | resonance | | |
|---|---|---|---|---|---|---|
| | image | spot means [counts] | signal/ noise*) | image | spot means [counts] | signal/ noise*) |
| I) Cy5-labelled IL6 (500ng/ml, 10 microL, 2h incubation) | 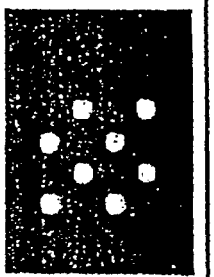 | 46 | 7.0 | 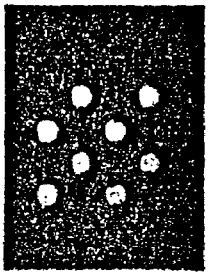 | 1100 | 69.2 |
| II) Cy5 labelled hCG (50ng/ml, 10 microL, 2h incubation) | 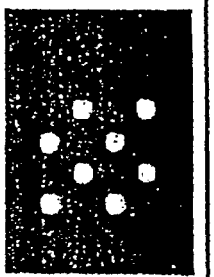 | 32 | 5.0 | 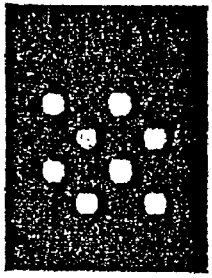 | 646 | 75.1 |
| III) Cy5-labelled with mixture of anti-IL6 (polyclonal)/IL6 (50ng/ml, 10 microL, 12h incubation) |  | 25 | 3.8 | 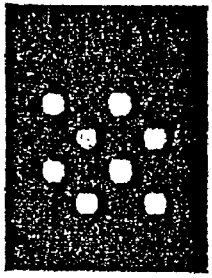 | 296 | 44.1 |

*) noise [counts] defined as standard deviation of image background

SENSOR PLATFORM, APPARATUS INCORPORATING THE PLATFORM AND PROCESS USING THE PLATFORM

This application is a continuation-in-part of U.S. patent application Ser. No. 09/609,846, filed Jul. 5, 2000 now U.S. Pat. No. 6,707,561.

This invention relates generally to the field of analysing samples and has particular, but not exclusive, application in the field of affinity sensing for example that known generally as DNA, protein, peptide and antibody chip technology. One aspect of the invention is concerned with a sensor platform which can be used to analyse samples. Another aspect of the invention is concerned with an apparatus which makes use of the sensor platform. A further aspect of the invention is concerned with the process for analysing samples which makes use of the platform.

Techniques for analysing two-dimensional arrays of samples are known. One such technique is known as an ELISA assay and is based upon the intense biochemical reaction between antibodies and antigens. Special mono or polyclonal antibodies are immobilised on substrates and react with complimentary species. Fluorophore labelled markers are added, activated via enzyme-linked antibodies, and the samples are irradiated with light in order to induce fluorescence. The fluorescence is detected and the intensity of the fluorescence is indicative of the affinity reaction.

Another known technique is that described in WO98/27430. In this a large number of different species are immobilised in an array on a substrate. The species are immobilised on the substrate by photolithographical means. Fluorophore labelled markers are added to the species. A sample is prepared and reacted with the immobilised species and the whole chip is scanned with a focused laser beam. Alternatively a sample is prepared and modified with fluorophore labelled markers and reacted with the immobilised species and the whole chip is scanned with a focussed laser beam. The fluorescent signals are detected by photodetectors and a 2D pattern is produced. Changes in this pattern between individual samples provide an indication of differences in gene expression and therefore provides information about pharmacology and toxicology.

Another known technique is that based on evanescent wave sensors. These make use of coherent laser light which is trapped in a very thin layer and creates so-called evanescent electromagnetic fields which extends for a small distance outside the actual physical sensor. This field can interact with molecules attached to the surface of the sensor. This evanescent excitation or interaction is limited to a region very close to the vicinity of the waveguide, typically 0.5 microns for visible light from the surface. The evanescent fields remain localised spatially and do not transfer their stored energy to other regions. The interaction of the laser light with the molecules can be used in a number of different ways. These include:
1 Detection of luminescence induced by the evanescent field.
2 Detection of changes in refractive index which occur when molecules of a sample bind to capture molecules.
3 Detection of surface plasmon resonance.

One particular sensor which uses an evanescent field is known as a planar waveguide sensor. The planar waveguide sensor comprises a planar substrate having formed thereon a thin wave guiding layer. Part of the wave guiding layer incorporates a grating onto which laser light is incident and from which the laser light is launched so that it propagates through the waveguide layer to a sensing region remote from the grating. The waveguide sensor can be either used in a mass sensitive mode (cf. 2, 3 above), or with superior sensitivity in combination with luminescence excitation and detection (cf. 1 above). Capture molecules are immobilised on the sensing area and the analyte (sample) is then brought into contact with the sensing area/capture molecules in the presence of added labelled molecules with similar affinity (competition). Alternatively, analyte molecules may bind to immobilised capture molecules and fluorescence labels are introduced by reaction of a further labelled species with the captured analyte molecules. Laser light launched into the waveguiding layer leads to evanescent excitation of the fluorophores which then allows the quantification of the analyte. The emitted fluorescence is detected and the intensity of the fluorescence provides an indication of the interaction that has occurred between affinity partners present in the analyte and the immobilised capture molecules. It should be noted that in this type of arrangement the laser radiation propagates inside the waveguide over relatively long distances and the coupling grating and the sensing areas are geometrically separated. (See WO 95/33197 and WO 95/33198).

EP-0 455 067 A2 describes a planar waveguide sensor exploiting the detecting principle of refractive index changes. The platform shallow grooves formed over the entire platform couple polarised, coherent light into the transparent waveguiding layer where it is coupled out after some distance. The angle of the outcoupled beam changes when analyte molecules bind to capture molecules.

Another example of the refractive index type is given in U.S. Pat. No. 5,738,825. The platform contains individual gratings being in contact with the wells of a microtiter plate.

EP 178 083 discloses Surface Plasmon Resonance (SPR) in which the energy of incoming photons is converted to electrical energy as a surface plasmon wave. The sensor architecture requires a metal layer in contrast to the platform of the present invention, and the amount of reflected light at the critical angle is, or approximates to, zero in contrast with the present invention in which the reflected intensity reaches almost 100%.

All the above techniques suffer from various disadvantages. Some are very slow because each sample has to be excited individually. Others such as the planar waveguide allow excitation of more than one sample at a time, but do not provide entirely reliable results because of fluorescence crosstalk between different capture elements and locally varying excitation light intensities due to losses of the waveguides and local variations of coupled power due to variations of grating coupling efficiencies.

The present invention is concerned with a technique which allows multiple samples to be analysed simultaneously in an extremely sensitive, reliable, and quantitative-manner.

In contrast to planar waveguide sensors, the present invention shows no luminescence crosstalk and local light intensities are well defined. The present invention allows true multiplexing, i.e. the transducer requires no stacked substructure (as is the case for planar waveguides) and can be seen as a universal platform, where, depending on the requirements, size and number of recognition elements can be varied within the technical feasible limitations, without requiring changes in the chip structure (corrugated areas and sensing areas are not separated as is the case for planar waveguides). In addition, the invention delivers about 100 fold stronger luminescence intensities compared to prior epifluorescence techniques. The experimental set-up is very simple and requires solely a simple adjustment of the angle of the incident light beam. The transducers described in the present invention, can be easily adapted to conventional fluorescence microscopes, confocal microscopes, and laser scanners. Furthermore, for transducers with a broad resonance width (defined as Full Width at Half Maximum, FWHM) and a resonance position at or close to normal incidence, angle adjustments are obsolete.

The production process of the platform is relatively simple (cheap) and the performance of existing systems (i.e. fluorescence scanners, microscopes, fluorescence microtiter plate readers, . . . ) can be easily increased by modest modifications of the respective set-ups.

According to a first aspect of the present invention there is provided a platform for use in sample analysis comprising an optically transparent substrate having a refractive index $(n_1)$, a thin, optically transparent layer, formed on one surface of the substrate, said layer having a refractive index $(n_2)$ which is greater than $(n_1)$, said platform incorporating therein one or multiple corrugated structures comprising periodic grooves which define one or multiple sensing areas or regions, each for one or multiple capture elements, said grooves being so profiled, dimensioned and oriented that either a) coherent light incident on said platform is diffracted into individual beams or diffraction orders which interfere resulting in reduction of the transmitted beam and an abnormal high reflection of the incident light thereby generating an enhanced evanescent field at the surface of the one or multiple sensing areas; or b) coherent and linearly polarised light incident on said platform is diffracted into individual beams or diffraction orders which interfere resulting in almost total extinction of the transmitted beam and an abnormal high reflection of the incident light thereby generating an enhanced evanescent field at the surface of the one or multiple sensing areas.

According to a second aspect of the present invention there is provided a platform comprising an optically transparent substrate having a refractive index (n1), a thin, optically transparent layer, formed on one surface of the substrate, said layer having a refractive index (n2) which is greater than (n1), said platform incorporating in the transparent layer a corrugated structure substantially over the entire platform, or multiple separate corrugated structures arranged on the platform, said structures comprising substantially parallel periodic grooves which are mono- or multi-diffractional which grooves represent one or multiple sensing areas or regions, wherein (a) the depth of the grooves is in the range of 3 nm to the thickness of the optically transparent layer,
(b) the thickness of the optically transparent layer is in the range of 30 to 1000 nm,
(c) the period of the corrugated structure is in the range of 200 to 1000 nm,
(d) the ratio of groove depth to the thickness of the optically transparent layer is in the range of 0.02 to 1, and
(e) the ratio of groove width to the period of the grooves is in the range of 0.2 to 0.8. The arrangement may be such that, in use, the grooves are so profiled, dimensioned and oriented that either a) coherent light incident on the platform is diffracted into individual beams or diffraction orders which interfere resulting in reduction of the transmitted beam and an abnormal high reflection of the incident light thereby generating an enhanced evanescent field at the surface of the one or multiple sensing areas; or b) coherent and linearly polarised light incident on said platform is diffracted into individual beams or diffraction orders which interfere resulting in almost total extinction of the transmitted beam and an abnormal high reflection of the incident light thereby generating an enhanced evanescent field at the surface of the one or multiple sensing areas.

As used herein, orientation is understood to mean that the electric field vector of the linearly polarised light is parallel or perpendicular to the grooves. As used herein, coherent light is understood to mean that the coherence length of the radiation, i.e. the spatial extent to which the incident beam has a defined phase relation, is large compared to the thickness of the platform.

The evanescent field decays exponentially within wavelength dimensions of the incident beam (less than 1 µm).

An important aspect of the present invention is the use of a platform in which so-called evanescent resonance can be created. Abnormal reflection is a phenomenon which has been described theoretically in the prior art for example in a paper entitled "Theory and applications of guided mode resonance filters" by SS Wang and R Magnusson in Applied Optics, Vol. 32, No 14, 10 May 1993, pages 2606 to 2613 and in a paper entitled "Coupling gratings as waveguide functional elements" by O. Parriaux et al, Pure & Applied Optics 5, (1996) pages 453–469. As explained in these papers resonance phenomena can occur in planar dielectric layer diffraction gratings where almost 100% switching of optical energy between reflected and transmitted waves occurs when the grooves of the diffraction grating have sufficient depth and the radiation incident on the corrugated structure is at a particular angle. In the present invention this phenomenon is exploited in the sensing area of the platform where that sensing area includes diffraction grooves of sufficient depth and light is caused to be incident on the sensing area of the platform at an angle such that evanescent resonance occurs in that sensing region. This creates in the sensing region an enhanced evanescent field which is used to excite samples under investigation. It should be noted that the 100% switching referred to above occurs with parallel beam and linearly polarised coherent light and the effect of an enhanced evanescent field can also be achieved with non-polarised light of a non-parallel focussed laser beam.

At resonance conditions the individual beams interfere in such a way that the transmitted beam is cancelled out (destructive interference) and the reflected beam interferes constructively giving rise to abnormal high reflection.

By choosing appropriate parameters for the above mentioned corrugated layer structure the excitation energy remains highly localized. Such structures are described in the literature as photonic band gap structures, materials with periodic spatial variations of their refractive index such that electromagnetic radiation cannot propagate in any direction. Photonic bandgap structures allow highly localized modes to appear, see e.g. the paper entitled "Localisation of One Photon States" by C. Adlard, E. R. Pike and S. Sarkar in Physical Review Letters, Vol. 79, No 9, pages 1585–87 (1997). Such structures exhibit extremely large propagation losses corresponding to a mode localisation in the µm regime.

The platform of the present invention can be considered as optically active in contrast to optically passive platforms constructed from e.g. a glass or polymer. Here, optically active means increasing the electromagnetic field of the excitation beam by energy confinement.

The substrate of the platform may be formed from inorganic materials such as glass, $SiO_2$, quartz, Si. Alternatively the substrate can be formed from organic materials such as polymers preferably polycarbonate (PC), poly(methyl methacrylate) (PMMA), polyimide (PI), polystyrene (PS), polyethylene (PE), polyethylene terephthalate (PET) or polyurethane (PU). These organic materials are especially preferred for point-of-care (POC) and personalized medical applications since glass is not accepted in such an environment. Plastics substrates can be structured (embossed) much more easily than glass. In one example the substrate is formed from glass.

The optically transparent layer may be formed from inorganic material. Alternatively it can be formed from organic material. In one example the optically transparent layer is a metal oxide such as $Ta_2O_5$, $TiO_2$, $Nb_2O_5$, $ZrO_2$, ZnO or $HfO_2$. The optically transparent layer is non-metallic.

Alternatively the optically transparent layer can be made of organic material such as polyamide, polyimide, polypropylene (PP), PS, PMMA, polyacryl acids, polyacryl ethers, polythioether, poly(phenylenesulfide), and derivatives thereof (see for example S S. Hardecker et al., J. of Polymer Science B: Polymer Physics, Vol. 31, 1951–63, 1993).

The depth of the diffraction grooves may be in the range 3 nm to the thickness of the optically transparent layer and preferably 10 nm to the thickness of the optically transparent layer e.g. 30 nm to the thickness of the optically transparent layer. The thickness of the optically transparent layer be in the range 30 to 1000 nm, e.g. 50 to 300 nm, preferably 50–200 nm, the period of the corrugated structure may be in the range 200 to 1000 nm, e.g. 200 to 500 mm, preferably 250–500 nm, the ratio of the groove depth to the thickness of the optically transparent layer may lie in the range 0.02 to 1 e.g. 0.25 to 1, preferably 0.3 to 0.7, and the ratio of the grooves width to the period of the grooves ("duty-cycle") may lie in the range 0.2 to 0.8, e.g. 0.4 to 0.6.

The grooves may be generally rectangular in cross-section. Alternatively, the grooves may be sinusoidal or of saw tooth cross-section. The surface structure may be generally symmetrical. Preferred geometries include rectangular, sinusoidal, and trapezoidal cross-sections. Alternatively, the grooves may be of saw tooth cross-section (blazed grating) or of other asymmetrical geometry. In another aspect the groove depth may vary, e.g. in periodic modulations.

The platform may be square or rectangular and the grooves may extend linearly along the platform so as to cover the surface. Alternatively the platform may be disc shaped and the grooves may be circular or linear.

The grooves may be formed on a surface of the substrate. Alternatively the grooves may be formed on a surface of the optically transparent layer. As a further alternative, grooves may be formed both on the surface of the substrate which is the interface and on the surface of the optically transparent layer.

The corrugated surface of a single sensing area may be optimized for one particular excitation wavelength and for one particular type of polarisation. By appropriate means, e.g. superposition of several periodic structures which are parallel or perpendicular one with another, periodic surface reliefs can be obtained that are suitable for multiple wavelength use of the platform ("multicolour" applications). Alternatively, individual sensing areas on one platform may be optimized for different wavelengths and/or polarization orientations.

The surface of the optically transparent layer may include one or a plurality of corrugated sensing areas which each may carry one or a plurality of capture elements.

Each capture element may contain individual and/or mixtures of capture molecules which are capable of affinity reactions. The shape of an individual capture element may be rectangular, circular, ellipsoidal, or any other shape. The area of an individual capture element is between 1 $\mu m^2$ and 10 $mm^2$, e.g. between 20 $\mu m^2$ and 1 $mm^2$ and preferably between 100 $\mu m^2$ and 1 $mm^2$. The capture elements may be arranged in a regular two dimensional array. The center-to-center (ctc) distance of the capture elements may be between 1 $\mu m$ and 1 mm, e.g. 5 $\mu m$ to 1 mm, preferably 10 $\mu m$ to 1 mm.

The number of capture elements per sensing area is between 1 and 1,000,000, preferably 1 and 100,000. In another aspect, the number of capture elements to be immobilized on the platform may not be limited and may correspond to e.g. the number of genes, DNA sequences, DNA motifs, DNA micro satelites, single nucleotide polymorphisms (SNPs), proteins or cell fragments constituting a genome of a species or organism of interest, or a selection or combination thereof. In a further aspect, the platform of this invention may contain the genomes of two or more species, e.g. mouse and rat.

The platform may include an adhesion promoting layer disposed at the surface of the optically transparent layer in order to enable immobilisation of capture molecules. The adhesion promoting layer may also comprise a microporous layer (ceramics, glass, Si) for further increasing assay and detection efficacy or of gel layers which either can be used as medium for carrying out the capture element immobilisation and sample analysis, thereby further increasing the assay and detection efficacy, or which allow separation of analyte mixtures in the sense of gel electrophoresis. The platform may be formed with a plurality of sensing areas or regions, each having its own diffractive grooves.

A feature of the platform of this invention is that light energy entering the optically transparent layer is diffracted out of the layer immediately due to the nature of the corrugated platform. Therefore no or negligible waveguiding occurs. Typically the propagation distance is 100 $\mu m$ or less, preferably 10 $\mu m$ or less. This is a very surprisingly short distance. The propagation distance is the distance over which the energy of the radiation is reduced to 1/e.

A third aspect of the invention provides apparatus for analysing samples comprising a platform according to said first or second aspect, means for generating a light beam and for directing the beam so that it is incident upon the platform at an angle which causes evanescent resonance to occur in the platform to thereby create an enhanced evanescent field in the sensing area of the platform, and means for detecting a characteristic of a material disposed on the sensing area of the platform. The range of angles suitable for creating a resonance condition is limited by the angle of total reflection for incident light on the platform. Preferred angles are less than 45°, e.g. 30° or less, e.g. 20° to 10° or below, e.g. 0.1° to 9.9°. The angle may equal or approximate normal incidence. The light generating means may comprise a laser for emitting a coherent laser beam. Other suitable light sources include discharge lamps or low pressure lamps, e.g. Hg or Xe, where the emitted spectral lines have sufficient coherence length, and light-emitting diodes (LED). The apparatus may also include optical elements for directing the laser beam so that it is incident on the platform at an angle $\theta$, and elements for shaping the plane of polarisation of the coherent beam, e.g. adapted to transmit linearly-polarised light. The angle $\theta$ may be defined by the expression $\sin\theta = n - \lambda/\Lambda$ where $\Lambda$ is a period of the diffractive grooves, $\lambda$ is the wavelength of the incident light and n is the effective refractive index of the optically transparent layer.

Examples of lasers that may be used are gas lasers, solid state lasers, dye lasers, semiconductor lasers. If necessary, the emission wavelength can be doubled by means of non-linear optical elements. Especially suitable lasers are argon ion lasers, krypton ion lasers, argon/krypton ion lasers, and helium/neon lasers which emit at wavelengths between 275 and 753 nm. Very suitable are diode lasers or frequency doubled diode lasers of semiconductor material which have small dimensions and low power consumption.

Another appropriate type of excitation makes use of VCSEL's (vertical cavity surface-emitting lasers) which may individually excite the recognition elements on the platform.

The detecting means may be arranged to detect luminescence such as fluorescence. Affinity partners can be labelled in such a way that Förster fluorescence energy transfer (FRET) can occur upon binding of analyte molecules to capture molecules. The maximum of the luminescence intensity might be slightly shifted relative to the position of highest abnormal reflection depending on the refractive index values of the layer system and the corresponding Fresnel Coefficients.

The samples may be used either undiluted or with added solvents. Suitable solvents include water, aqueous buffer solutions, protein solutions, natural or artificial oligomer or polymer solutions, and organic solvents. Suitable organic solvents include alcohols, ketones, esters, aliphatic hydrocarbons, aldehydes, acetonitrile or nitrites.

Solubilisers or additives may be included, and may be organic or inorganic compounds or biochemical reagents such as diethylpyrocarbonate, phenyl, formamide, SSC (sodium citrate/sodium chloride), SDS (Sodiumdodecylsulfate), buffer reagents, enzymes, reverse transcriptase, RNAase, organic or inorganic polymers.

The sample may also comprise constituents that are not soluble in the solvents used, such as pigment particles, dispersants and natural and synthetic oligomers or polymers.

The luminescence dyes used as markers may be chemically or physically, for instance electrostatically, bonded to one or multiple affinity binding partners (or derivatives thereof) present in the analyte solution and/or attached to the platform. In case of naturally-occurring oligomers or polymers such as DNA, RNA, saccharides, proteins, or peptides, as well as synthetic oligomers or polymers, involved in the affinity reaction, intercalating dyes are also suitable. Luminophores may be attached to affinity partners present in the analyte solution via biological interaction such as biotin/avidin binding or metal complex formation such as HIS-tag coupling.

One or multiple luminescence markers may be attached to affinity partners present in the analyte solution, to capture elements immobilized on the platform, or both to affinity partners present in analyte solution and capture elements immobilized at the platform, in order to quantitatively determine the presence of one or multiple affinity binding partners. The spectroscopic properties of the luminescence markers may be chosen to match the conditions for Förster Energy Transfer or Photoinduced Electron Transfer. Distance and concentration dependent luminescence of acceptors and donors may then be used for the quantification of analyte molecules.

Quantification of affinity binding partners may be based on intermolecular and/or intramolecular interaction between such donors and acceptors bound to molecules involved in affinity reactions. Intramolecular assemblies of luminescence donors and acceptors covalently linked to affinity binding partners, Molecular Beacons (S. Tyagi et al., Nature Biotechnology 1996, 14, 303–308) which change the distance between donor and acceptor upon affinity reaction, may also be used as capture molecules or additives for the analyte solution. In addition, pH and potentially sensitive luminophores or luminophores sensitive to enzyme activity may be used, such as enzyme mediated formation of fluorescing derivatives.

Transfluorospheres or derivatives thereof may be used for fluorescence labelling, and chemi-luminescent or electroluminescent molecules may be used as markers.

Luminescent compounds having luminescence in the range of from 400 nm to 1200 nm which are functionalised or modified in order to be attached to one or more of the affinity partners, such as derivatives of polyphenyl and heteroaromatic compounds stilbenes, coumarines, xanthene dyes, methine dyes, oxazine dyes, rhodaines, fluoresceines, coumarines, stilbenes, pyrenes, perylenes, cyanines, oxacyanines, phthalocyanines, porphyrines, naphthalopcyanines, azobenzene derivatives, distyryl biphenyls, transition metal complexes e.g. polypyridyl/ruthenium complexes, tris(2,2'-bipyridyl)ruthenium chloride, tris (1,10-phenanthroline)ruthenium chloride, tris(4,7-diphenyl-1,10-phenanthroline) ruthenium chloride and polypyridyl/phenazine/ruthenium complexes, such as octaethyl-platinum-porphyrin, Europium and Terbium complexes may be used as luminescence markers.

Suitable for analysis of blood or serum are dyes having absorption and emission wavelength in the range from 400 nm to 1000 nm. Furthermore luminophores suitable for two and three photon excitation can be used.

Dyes which are suitable in this invention may contain functional groups for covalent bonding, e.g. fluorescein derivatives such as fluorescein isothiocyanate. Also suitable are the functional fluorescent dyes commercially available from Amersham Life Science, Inc. Texas. and Molecular Probes Inc.

Other suitable dyes include dyes modified with deoxynucleotide triphosphate (dNTP) which can be enzymatically incorporated into RNA or DNA strands. Further suitable dyes include Quantum Dot Particles or Beads (Quantum Dot Cooperation, Palo Alto, Calif.) or derivatives thereof or derivatives of transition metal complexes which may be excited at one and the same defined wavelength, and derivatives show luminescence emission at distinguishable wavelengths.

Analytes may be detected either via directly bonded luminescence markers, or indirectly by competition with added luminescence marked species, or by concentration-, distance-, pH-, potential- or redox potential-dependent interaction of luminescence donors and luminescence/electron acceptors used as markers bonded to one and/or multiple analyte species and/or capture elements. The luminescence of the donor and/or the luminescence of the quencher can be measured for the quantification of the analytes.

In the same manner affinity partners can be labelled in such a way that electron transfer or photoinduced electron transfer leads to quenching of fluorescence upon binding of analyte molecules to capture molecules.

Appropriate detectors for luminescence include CCD cameras, photomultiplier tubes, avalache photodiodes, photodiodes, hybrid photomultiplier tubes.

The detection means can be arranged to detect in addition changes in refractive index.

The incident beam may be arranged to illuminate the sensing area or all sensing areas on one common platform. Alternatively the beam can be arranged to illuminate only a small sub-area of the sensing area to be analysed and the beam and/or the platform may be arranged so that they can undergo relative movement in order to scan the sensing area of the platform.

Accordingly the detecting means may be arranged in an appropriate way to acquire the luminescence signal intensities of the entire sensing area in a single exposure step. Alternatively the detection and/or excitation means may be arranged in order to scan the sensing areas stepwise.

The apparatus may include a cartridge for location against the sensing area of the platform to bring a sample into contact with the sensing area. The cartridge may contain further means in order to carry out sample preparation, diluting, concentrating, mixing, bio/chemical reactions, separations, in a miniaturised format (see WO 97/02357). The apparatus may include a microtiter type device for containing a plurality of samples to be investigated.

A fourth aspect of the present invention provides a process for analysing a sample or samples which comprises bringing the sample into contact with the sensing area of a platform according to said first or second aspect, irradiating the platform with a light beam such that evanescent resonance is caused to occur within the sensing area of the platform and detecting radiation emanating from the sensing area. The method may comprise adding fluorescent inducing material to the samples under investigation and sensing fluorescence induced in said samples by excitation of the samples by the enhanced evanescent field. Alternatively the method may comprise adding fluorescence inducing or quenching material to the samples under investigation and/or transfer of the samples under investigation into fluorescing or quenching derivatives and sensing fluorescence induced by said samples bound at the sensing platform by excitation with the enhanced evanescent field.

It is believed to be a novel and inventive concept to provide a sensor platform in which each sensing area or region has attached thereto more than one type of capture element or molecule. This concept applies whether the platform is designed for evanescent resonant mode or a more conventional mode such as waveguiding. Thus, according to another aspect of the present invention there is provided a platform for use in a sample analysis, said platform having one or more sensing areas or regions, each for receiving a capture element or elements which when the platform is irradiated with coherent light can interact to provide an indication of an affinity reaction, wherein each capture element includes two or more types of capture molecule.

The above-described embodiments of this invention contemplate light polarised parallel with the longitudinal axis of the grooves of the platform, giving rise to "TE" excitation, or light polarised perpendicular to the longitudinal axis of the grooves of the platform, giving rise to "TM" excitation. Further, light may be incident either onto the corrugated, optically transparent, high refractive index layer side of the platform ("chip") or onto the other side of the platform, i.e. onto the optically transparent substrate side.

The nature of polarisation and aspects of excitation of TE and TM modes are discussed in *Guided Wave Optoelectronics*, Ed. T. Tamir, 1988, Springer Verlag, specifically the Chapter entitled *Theory of Optical Waveguides*, Author: H. Kogelnik, the contents of which are incorporated herein by reference.

The present applicants have found that even greater amplification can be obtained by exploiting the abnormal reflection geometry provided by TM excitation compared to TE excitation.

A further increase in sensitivity may be obtained when the light incident on the platform is directed onto the optically transparent substrate. This may be attractive for e.g. fluorescence laser scanners.

In a further aspect, therefore, this invention provides a platform, apparatus or detection method as described herein adapted to TM excitation.

It will be appreciated that varying degrees of polarisation of the incident light beam may be employed, depending e.g. on field of application and resources available or required. The abnormal reflection and/or fluorescence enhancement described herein is observed preferably from the linearly polarised component of the incident light. Thus the light incident on the platform may be e.g. substantially linearly polarised or circularly or elliptically polarised.

Increases of signal intensity amplification have been detected by a factor of up to around 5 to 10 using TM excitation over TE excitation.

In a further aspect, this invention provides a platform, apparatus or detection method as described herein wherein the light beam is irradiated onto the transparent substrate side of the platform. The applicants have found that several times greater signal intensity, e.g. a factor of 5 to 7, may be obtained when irradiating the platform onto the substrate side instead of onto the corrugated, optically transparent, high refractive index layer side of the platform.

An increase in signal intensity amplification by a factor of around 50 may be obtained by employing TM excitation with the light beam incident onto the substrate side compared with TE excitation and the light beam incident onto the corrugated, optically transparent, high refractive index layer side of the platform.

The invention will be described now by way of example only with particular reference to the accompanying drawings. In the drawings:

FIG. 10 shows fluorescence images and data obtained using the present platform under epifluorescence and resonance conditions as described in Example 6;

The invention will be described in terms of the determination of luminescence excited in samples. This determination involves the use of a sensor platform which constitutes one aspect of the present invention, but it will be appreciated that the use of such a platform is not necessarily restricted to the particular application to be described. Before describing the platform in detail a description will be given in general terms of the way in which the platform can be used to determine luminescence of samples.

The following are definitions of terms which will be used in the description:

Platform: a whole transducer/chip containing one or a plurality of sensing areas Sensing area: a whole corrugated area capable of creating an evanescent field by a resonance effect and containing one or a plurality of capture elements Capture element: an individual sensing spot containing one or a variety of species of capture molecules Capture molecule: an individual molecule capable of an affinity reaction Counts: signal intensity measured over a predetermined time interval. This time interval is one second unless otherwise stated.

In the following examples all temperatures are in degrees Centigrade and are uncorrected.

Figure 1:
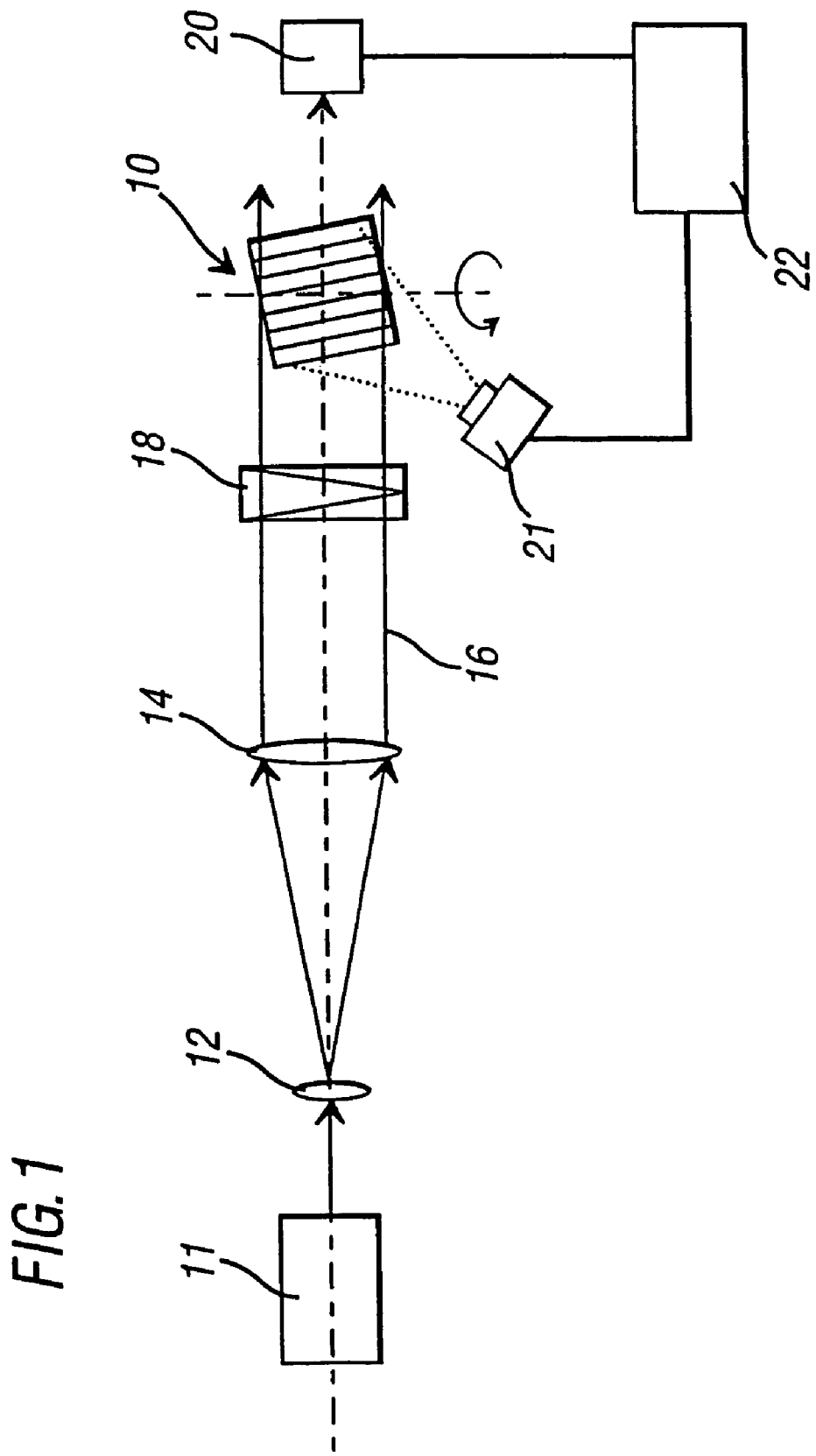
FIG. 1 is a schematic illustration of a quality control apparatus for analysing the optical parameters and the evanescent resonance condition of a platform in accordance with the present invention.

Referring to FIG. 1 a platform in accordance with an aspect of the present invention is shown at (10) and can receive coherent light from a laser (11), the laser light having been expanded by a set of lenses (12, 14) which produce an expanded and parallel beam (16), and polarised by a polariser (18). As will be explained in more detail later, the platform (10) has a sensing area to which are attached capture molecules. The wavelength of the light will typically be in the range UV to NIR range, preferably between 350 nm to 1000 nm.

The apparatus also includes a detector (20) which can detect light transmitted through the platform (10), a CCD camera (21) to detect the reflected light and a data processing unit (22).

In use of the apparatus a highly parallel, expanded, coherent, linearly polarised, laser beam (16) is caused to be incident on the sensing area of the platform (10) and light transmitted through the platform is sensed by detector (20) and the reflected light is recorded by the CCD camera (21). The diameter of the expanded excitation beam exceeds the size of the platform (10). The angle of incidence of the beam on the platform is adjusted by rotation of the platform until the detector (20) detects effectively no light being transmitted through the platform. This indicates the existence of a resonance position at which evanescent resonance is occurring in the sensing area of the platform. Under this condition, the reflected light intensity recorded by the camera (21) reaches a maximum and the data from the camera is acquired by the data processing unit (22) for processing.

Figure 2:
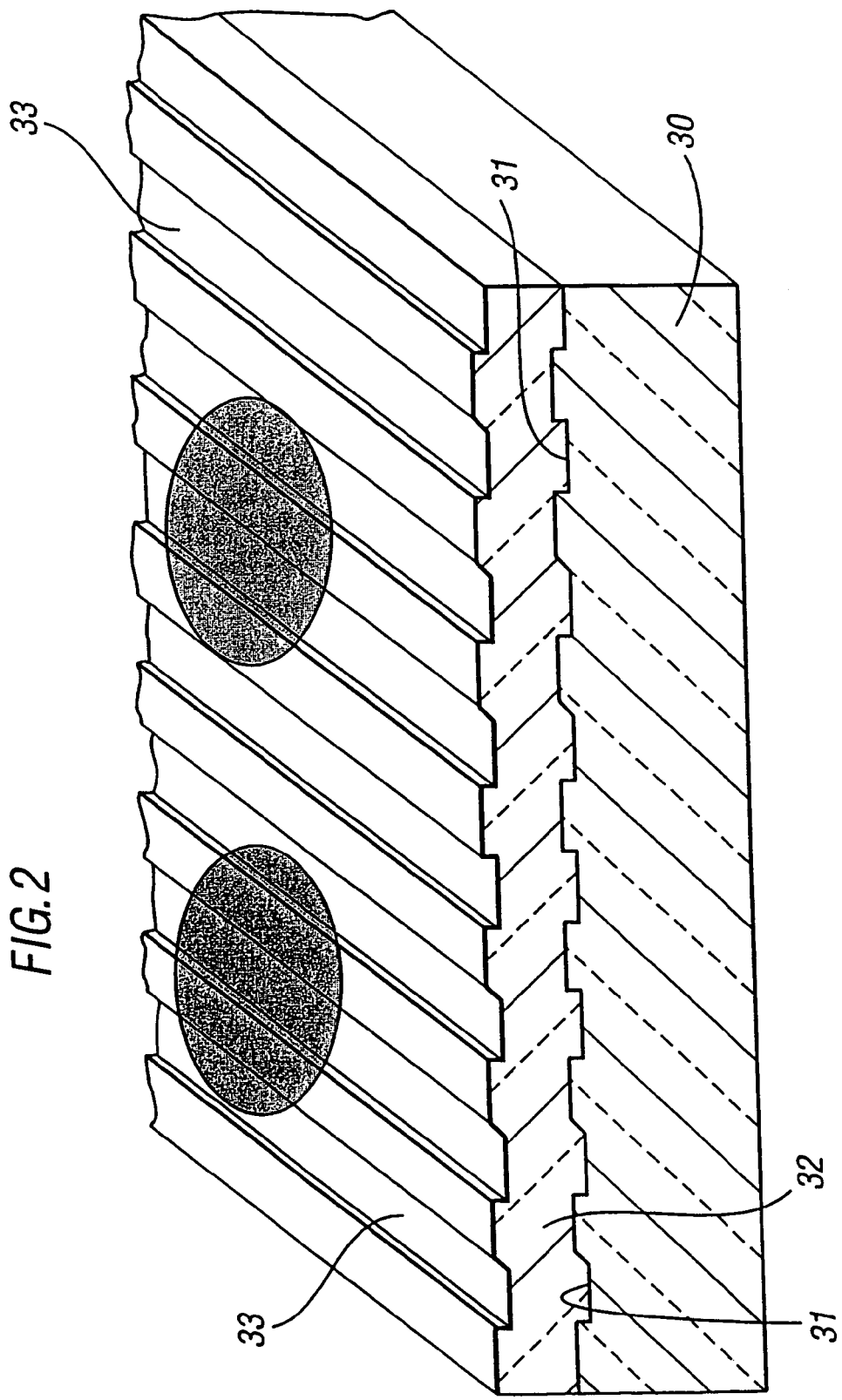
FIG. 2 is a schematic illustration of a sensor platform in accordance with the present invention.

Turning now to FIG. 2 of the drawings, an embodiment of the platform (10) comprises a glass substrate (30) into the top surface of which has been etched a plurality of grooves (31). A layer of optically transparent metal oxide (32) is deposited on the upper surface of the substrate (30) and that layer (32) also has formed therein grooves (33). The substrate (30) can for example be formed from glass such as glass AF45 produced by Schott and typically has a thickness of 0.5 mm–1.0 mm. It will be appreciated that other organic or inorganic materials can be used for the substrate provided that it is optically transparent.

The optically transparent layer is a dielectric transparent metal oxide film such as $Ta_2O_5$ with a high refractive index of approximately 2.2 at a wavelength of 633 nm, i.e. significantly higher than the refractive index of the substrate. The thickness of this layer will typically be in the range 50 to 200 nm or greater e.g. 50 to 300 nm. The corrugated structures (31) and (33) have a period in the range of 200–1000 nm, e.g. 200 to 500 nm, typically 250–500 nm. The depth of the corrugated structures/diffraction grooves may be in the range 3 nm to the thickness of the optically transparent layer, preferably 10 nm to the thickness of the optically transparent layer. The metal oxide can be any of a number of examples such as $Ta_2O_5$, $TiO_2$, $Nb_2O_5$, $ZrO_2$, ZnO, or $HfO_2$.

In a platform such as that shown in FIG. 2, when a parallel beam of polarised laser light is incident thereon at a particular angle of incidence, an effect known as abnormal reflection occurs within the layer (32). When this effect occurs substantially no light is transmitted through the platform (10) and effectively all the light is reflected within the layer (32) so that the coherent laser light is confined to the very thin layer (32) of metal oxide. The resulting high laser field leaks partially out of the layer (32) creating an evanescent field which evanescently excites fluorescent material which is on the surface or in the close vicinity of the layer (32). It should be noted that this resonance condition can be achieved only when diffractive grooves (31, 33) having a particular depth or greater are employed and it should also be noted that the radiation losses of such a corrugated structure are very high so that effectively no waveguiding of any electromagnetic radiation in the preferred wavelength range occurs within the layer of metal oxide (32). It is preferred that the depth of the grooves be at least 10 nm but the evanescent resonance starts to build up with shallower grooves. However, provided that the sample to be investigated is in the vicinity of the layer (32) at which the resonance is created the enhanced evanescent field can be used to excite luminescence such as fluorescence in the sample.

An important feature of the present platform is that the amplitude of this evanescent field at resonance position is significantly greater than that of the prior art arrangements (epifluorescence corresponding to off-resonance condition) by an order of approximately 100.

This means that the intensity of luminescence, e.g. fluorescence, which can be created from samples is also increased by a factor of 100. The function of the platform can be viewed in terms of the diffractive structure acting as a volume grating which diffracts light and that the diffractive beams interfere creating a resonance condition where the light reflected from the first interface and light reflected from the top interface that is the upper surface of the layer (32) interfere constructively giving rise to reflection maxima. Under resonance conditions, the laser energy is substantially confined to the thickness of the thin layer (32) thereby increasing the electrical field strength. For a given laser wavelength and period of the corrugated structure, the resonance is angle-dependent. The angle dependent resonance typically has a width at half maximum height (FWHM) of $>0.1°$ preferably $0.5°$ or greater e.g. $1.0°$ or greater. This resonance width is dependent upon the depth of the grooves, the duty cycle and geometry of the corrugated structure. Compared to coupling behaviour of a waveguide grating, the FWHM of the resonance described is greater by many orders of magnitude.

It will be appreciated that the diffraction grooves (31, 33) can be formed on the platform by appropriate conventional techniques. One way of achieving this is to etch the grooves by a photographical technique. In this, a photoresist composition is deposited on the surface of the substrate to a depth of approximately 1 µm, a periodic structure corresponding to the groove formation is then written into the resist either by two beam interferometry/holography or by use of a phase mask and then the resist is etched with a reactive ion etching technique using argon gas and finally the residual photoresist material is stripped from the surface. This technique can be used for forming both grooves (31) and grooves (33). Other ways of incorporating the corrugated structures include embossing, electron beam writing, laser ablation, LIGA process.

In order to prepare a platform of the type described with reference to FIG. 2 so that it can be used in a measurement such as that illustrated in FIG. 6, a number of procedures should be followed.

The first step is to clean the platform to remove impurities from the platform surface. The cleaning procedure can be achieved by a number of means, for example by means of an ultraviolet cleaner, by plasma cleaning, or by chemical cleaning using materials such as acids, bases, solvents, gases and liquids.

Once the platform has been cleaned the next step is to apply to the surface of the metal oxide layer a layer of an adhesion promoting agent. This layer is applied to the platform since capture elements which are to be deposited on the platform might not readily adhere to the metal oxide layer itself. There are several ways in which this layer can be formed. One way is to form a layer of a network of silane molecules and another way is to use what are known as self-assembled monolayers (SAM). These are known techniques which will be apparent to the person skilled in the art. Silanisation for example which can involve a liquid or gas phase is described in Colloids and Interface Science 6, L Boksanyi, O Liardon, E Kovats, 1976, 95–237. The formation of self-assembled monolayers is described for example in "Ultra thin organic films" by Abraham Ulman, 1991, Academic Press inc. In addition, there are further methods available for the immobilisation of capture elements such as chemical modification of the chip surface with reactive groups and of the capture molecules with appropriate linkers (U. Maskos and E. M. Southern, Nucleic Acids Research 1992, vol. 20, 1679–84)

modification of surface and capture molecules with photoreactive linkers/groups (WO 98/27430 and WO 91/16425)

Immobilisation via coulombic interaction (EP 0 472 990 A2)

coupling via tags (for instance proteine-tag, HIS-tag) in chelating reactions and various further methods, for instance as described in Methods in Enzymology Academic Press, New York, Klaus Mosbacher (ed.), Vol. 137, Immobilised enzymes and Cells, 1988.

Plasma induced immobilization/generation of adhesion promoting layers containing functional/reactive groups, which enable direct coupling of capture molecules or derivatized capture molecules, or indirect coupling of capture molecules or derivatized capture molecules via chemical linkers or photochemical linkers.

An adhesion promoting layer can for example be produced by silanization with 3-(glycidoxypropyl)trimethoxysilane (GOPTS). Compounds containing nucleophilic groups such as amines can react with the epoxy function of the silane in order to be covalently immobilized. Such a silanization can therefore e.g. be used for immobilization of antibodies which contain multiple amino groups since antibodies consist of amino acids. In addition, DNA/RNA/PNA strands as capture molecules can also be modified with amino groups in order to attach these capture molecules covalently at the platform, as shown in application Example 4 (SNP discrimination). In this example, oligonucleotides with amino function have been covalently immobilized at the surface of the platform. However, other types of capture molecules can be modified for this purpose.

In addition, an adhesion promoting layer can be further chemically modified in order to alter the surface properties. For example, a GOPTS-silanized platform can be reacted with functionalized saturated or unsaturated organic/hetero-organic/inorganic molecules/derivatives in order to manipulate hydrophobic/hydrophilic balance of the platform, i.e. change the contact angle of the platform. Furthermore, ionic or potentially ionic compounds can be used to create positive or negative charges at the surface of the platform. Capture molecules can be bound either covalently or by physisorption or by coulombic interaction of charged molecules or by a mixture thereof to such modified surfaces/platforms. This is demonstrated in application Example 2 below, where 3-amino-1-propanol is used to modify the surface characteristics of the GOPTS-silanized platform in a second reaction step in order to immobilize DNA/RNA/PNA capture molecules. In this example the nitrogen (amine group) introduced at the surface of the platform is quaternized by protons and provides therefore positive charges which interact with negative charges of the DNA (polyelectrolyte nature). Instead of 3-amino-1-propanol also other organic derivatives of amines, e.g. aliphatic amines, or branched aliphatic amines, or amines containing aromatic or non-aromatic cyclic structures, or amines containing heteroatoms, or amines containing functional groups, or amines containing combinations thereof can be used for the immobilization of capture molecules, e.g. DNA/RNA/PNA strands.

Functionalized organic molecules can be used which provide hydrocarbon chains to render the platform more hydrophobic, polar groups can be used to render the platform more hydrophilic, or ionic groups, or potentially ionic groups can be used to introduce charges. For instance Polyethyleneglycol (PEG) or derivatives thereof can be used to render the platform hydrophilic, which prevents non-specific absorption of proteins to the platform/surface.

Reactive or photoreactive groups may be attached to the surface of the platform which may serve as anchor groups for further reaction steps.

A SAM as adhesion promoting layer suitable for immobilization of antibodies can be obtained by treatment of the platform with amphiphilic alkylphosphates (e.g. stearyl phosphate). The phosphate headgroup reacts with the hydroxy groups at the surface of the platform and leads to the formation of an ordered monolayer of the amphiphilic alkylphoshates. The hydrophophic alkyl chains render the surface of the platform hydrophobic and thus enable the physisorption of antibodies, as shown in application Example 6 (multiplexed immunoassays).

A SAM may also be used for the immobilization of other capture molecules, e.g. for DNA/RNA/PNA strands. In this case, amphiphilic phosphates/phosphates modified e.g. with amine groups or epoxy groups can also be used. The capture molecules can be either coupled directly to the SAM, e.g. to an amine-modified SAM, or after the platform has been reacted with organic derivatives of amines, e.g. aliphatic amines, or branched aliphatic amines, or amines containing aromatic or non-aromatic cyclic structures, or amines containing hetero-atoms, or amines containing functional groups, or amines containing combinations thereof, or any other organic, hetero-organic, and/or inorganic molecules (e.g. epoxy modified SAM).

An adhesion promoting layer may consist of multiple layers in order to manipulate surface characteristics, e.g. hydrophobicity, contact angle, charge density. In addition, a layer attached to the platform with any of above mentioned methods may provide or introduce chemical functionality with is required either for the next, subsequent layer, or for the coupling of capture molecules or derivatized capture molecules. An attachment of chemical linker molecules or photochemical linker molecules can also be seen as an intermediate layer which enables the attachment of capture molecules to the platform.

This controlled combination of layers/molecules with different functionalities in general is attributed as Supramolecular Chemistry (J-M. Lehn, Supramolecular chemistry —Scope and perspectives. Molecules, supermolecules, and molecular devices, (Nobel Lecture, 8.12.1987), Angew. Chem. Int. Ed. Engl., 27, 89, 1988.). The obtained supramolecular structure provides a functionality which differs from the functionality of the individual molecules used for the individual layers. For the present invention, an intermediate layer can also introduce luminophors into such a layer system, which can either be used as energy donor or energy acceptor/quencher in the sense of Förster Energy Transfer (FRET) or photoinduced electron transfer, or potential sensitive luminophors, before capture molecules or modified capture molecules are attached to the platform.

For the above-described methods of surface treatment, the following organic or inorganic molecules and derivatives thereof can be used: amines, modified amines, jeffamines, aliphatic amines, alcohols, acids, aldehydes, ketones, amides, anhydrides, phosphates, phosphonates, sulfates, sulfonates, thiols, hetero-atom containing compounds, aromatic and aliphatic organic functionalized molecules, aromatic and aliphatic hetero-organic molecules, natural and artificial polymers, silanes, molecules modified with chemical or photochemical active groups, derivatives thereof and functionalized, e.g. omega-functionalized derivatives of the listed species.

In principle, for the build-up of layer structures consisting of one or multiple layers, chemical reactive groups and/or chemical groups having special physical or electro chemical properties (e.g. charges) are required for the used molecules with all of the above described surface treatments.

Either chemical/photochemical interactions (e.g. addition, nucleophilic/electrophilic substitution, radical reaction, condensation, reactions with organic/hetero-organic/inorganic carbonyl derivatives, or photo-induced reactions, or thermo-induced reactions, Lewis acid/base concept), and/or physical/electrochemical interaction (e.g. Coulomb-interaction, hydrophobic/hydrophilic interaction), and/or biologic interaction (e.g. antigene/antibody, hybidization, Streptavidin/Avidin-Biotine interaction, agonist/antagonist interaction), and/or photochemical/photophysical interaction may be employed for coupling between molecules/components incorporated into such a layer system/adhesion promoting layer.

Adhesion promotion can also be achieved by deposition of microporous layers or gels on the surface of the platform, the surface characteristics/functionality of the microporous layers or gels facilitating deposition of capture elements shortening the required incubation time and enhancing sensitivity of the subsequent measures. The microporous layers can comprises organic compounds such as polymers, monomers, molecular assemblies and supra molecular assemblies or it can comprise inorganic compounds such as glass, quartz, ceramic, silicon and semiconductors.

An adhesion-promoting layer may be produced by silanisation e.g. using 3-(glycidoxypropyl)trimethoxysilane (GOPTS). The adhesion promoting layer may be further chemically modified in order to alter the surface properties. For example, a GOPTS-silanized platform may be reacted with functionalized saturated or unsaturated organic molecules in order to manipulate the hydrophobic/hydrolilic balance of the platform, and thereby altering the contact angle of the platform.

Once the adhesion promoting layer has been formed on the platform an additional cleaning step or steps may be necessary to remove excess chemicals used in the preparation of such a layer. After that cleaning the platform is then ready to receive capture elements.

A two dimensional array of capture or recognition elements is formed on the 3-D surface of the adhesion promoting layer previously deposited on the platform. The array of capture elements can be deposited in a variety of ways. Techniques which can be used to deposit capture elements include ink jet printers which have piezoelectric actuators, electromagnetic actuators, pressure/solenoid valve actuators or other force transducers; bubble jet printers which make use of thermoelectric actuators; or laser actuators; ring-pin printers; pin tool-spotters; on-chip-synthesis such as that described in WO90/03382 or WO92/10092; very large scale immobilised polymer synthesis (VLSIPS) such as that described in WO98/27430; photoactivation/photodeprotection of special design photoreactive groups anchored at the surface of the adhesion promoting layer; microcontact printing; microcontact writing pens; drawing pen or pad transfer/ stamping of capture elements; microfluidics channels and flowcells made by casting from polymer such as PMMA masters for example using PDMS (polydimethoxysilane) or by micromechanical or mechanical means, or made by etching techniques for local delivery of capture elements; structuring of capture elements by photoablation; or deposition of capture elements onto gel pads using one of the previously mentioned techniques or any other photoimmobilisation technique.

The capture or recognition elements which can be deposited onto the platform are many and varied. Generally speaking the capture molecules used should be capable of affinity reactions. Examples of recognition or capture molecules which can be used with the present platform are as follows:

nucleotides, oligonucleotides (and chemical derivatives thereof)
DNA (double strand or single strand)
  a) linear (and chemical derivatives thereof)
  b) circular (e.g. plasmids, cosmids, BACs, ACs)
total RNA, messenger RNA, cRNA, mitochondrial RNA, artificial RNA, aptamers PNA (peptide nucleic acids)
Polyclonal, Monoclonal, recombinant, engineered antibodies, antigenes, haptens, antibody FAB subunits (modified if necessary)
proteins, modified proteins, enzymes, enzyme cofactors or inhibitors, protein complexes, lectines, Histidine labelled proteins, chelators for Histidine-tag components (HIS-tag), tagged proteins, artificial antibodies, molecular imprints, plastibodies membrane receptors, whole cells, cell fragments and cellular substructures, synapses, agonists/antagonists, cells, cell organelles, e.g. microsomes small molecules such as benzodiazapines, prostaglandins, antibiotics, drugs, metabolites, drug metabolites natural products carbohydrates and derivatives natural and artificial ligands steroids, hormones peptides native or artificial polymers molecular probes natural and artificial receptors and chemical derivatives thereof chelating reagents, crown ether, ligands, supramolecular assemblies indicators (pH, potential, membrane potential, redox potential)

tissue samples (tissue micro arrays)

The activity or density of the capture molecules can be optimised in a number of ways. The platform with the capture elements deposited thereon can be incubated in saturated water vapour atmosphere for a defined period in order to rehydrate the printed loci. This optimises the density of the capture molecules, i.e. increases available binding sites per unit area. Subsequently the incubated chips can be baked for a defined period, say 1 minute at 80° C. for cDNA capture molecules. The platform can be washed by wetting with a small amount of pure water or any other suitable liquids or solutions to avoid cross contamination of the capture elements by excess unbound material. After these procedures, the prepared platform can be stored in a dessicator until use. Prior to use of the chip, an additional washing procedure with 0.1 to 10 ml hybridization buffer or other suitable solutions/liquids may be required to reactivate/rehydrate the dried capture elements and to further remove excess unbound capture elements/buffer residues. In the case of DNA capture molecules, the washing procedure has found to be most effective when performed at a temperature between 50 and 85° C.

Process steps for the chip handling can be automated by using hybridization stations such as e.g. the GeneTAC Hybridization station from Genomic Solutions Inc., Michigan, US.

The particular measurement technique to be described is that involving luminescence in particular fluorescence. In carrying out a measurement, a sample to be investigated is placed on the sensing area of the platform on which the capture elements have been provided. In order to achieve fluorescence, fluorophores are added to the system prior to the measurement being taken. The fluorophores can be added to the sample for example as labelled affinity partners although it is also possible to attach fluorophores to the capture elements on the platform. The measurements are based upon the fact that fluorescent emission from the capture elements containing labelled capture molecules and/or from labelled affinity partners is altered by its interaction with the analyte or sample under investigation. Labels of different excitation and emission wavelength can be used, there being one or several different labels, label 1 being for a control experiment and label 2 for the experiment.

Figure 3:
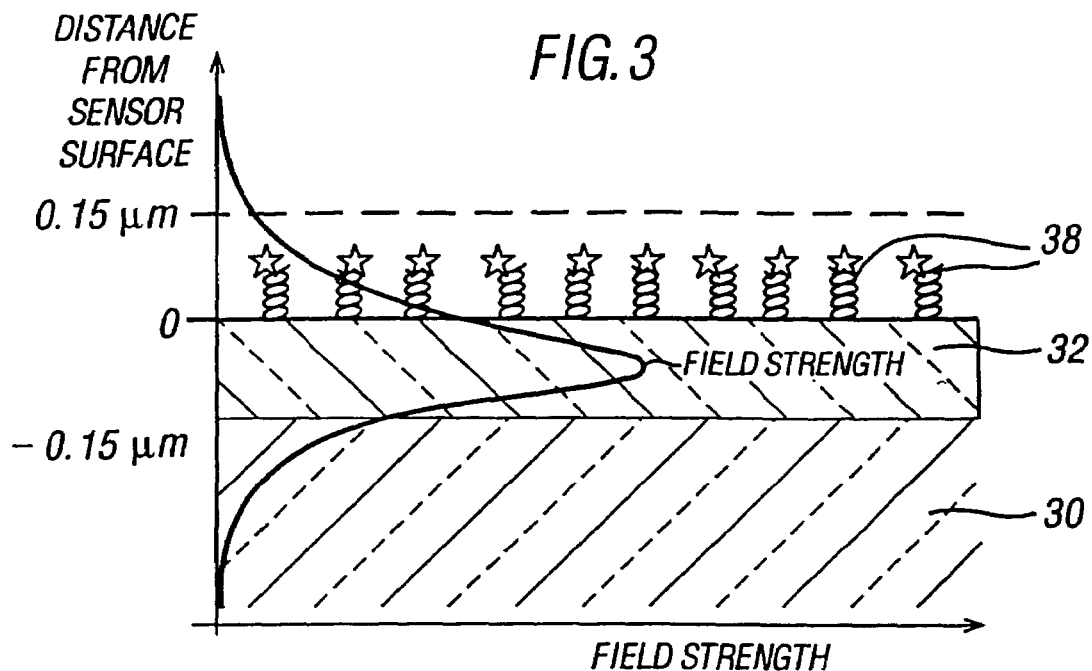
FIG. 3 is a schematic view showing the evanescent field profile in relation to the platform.

FIG. 3 shows schematically the energy profile of the evanescent field at resonance position and how it extends beyond the surface of the metal oxide layer (32) so that it can excite fluorophores in the close vicinity of the surface of the sensing area, e.g. fluorophores attached to capture molecules or fluorophores attached to molecules bound to the capture molecules (38). The evanescent field decreases exponentially to zero within approximately one micron.

It will be appreciated that in carrying out an analysis one or multiple measurements are made. One can be background measurement prior to the sample being brought into contact with the capture elements. A second measurement can be made with/after the sample has been brought in contact with the capture elements. For comparison of multiple samples, for instance "control" and "treated" sample in gene expression experiments, the chip can be regenerated after the "control" experiment as described in the application example 2, and a further background measurement and a measurement after/with the "treated" sample (was) applied to the chip can be registered. To gain information regarding the reaction kinetics of the affinity partners, a complete set of measurements can be recorded as a function of incubation time and/or post-wash time. A typical arrangement for such a measurement is shown in FIG. 6. The platform shown in FIG. 2 is adjusted to the angle at which evanescent resonance is achieved and a measurement of the fluorescence emitted from the surface of the platform is made using the CCD camera (66). This provides an indication of the fluorescence emitted from each position on the array of capture elements deposited on the platform. This can be analysed to deduce the affinity of the reactions which have occurred between the capture elements and the sample under investigation.

Figure 6:
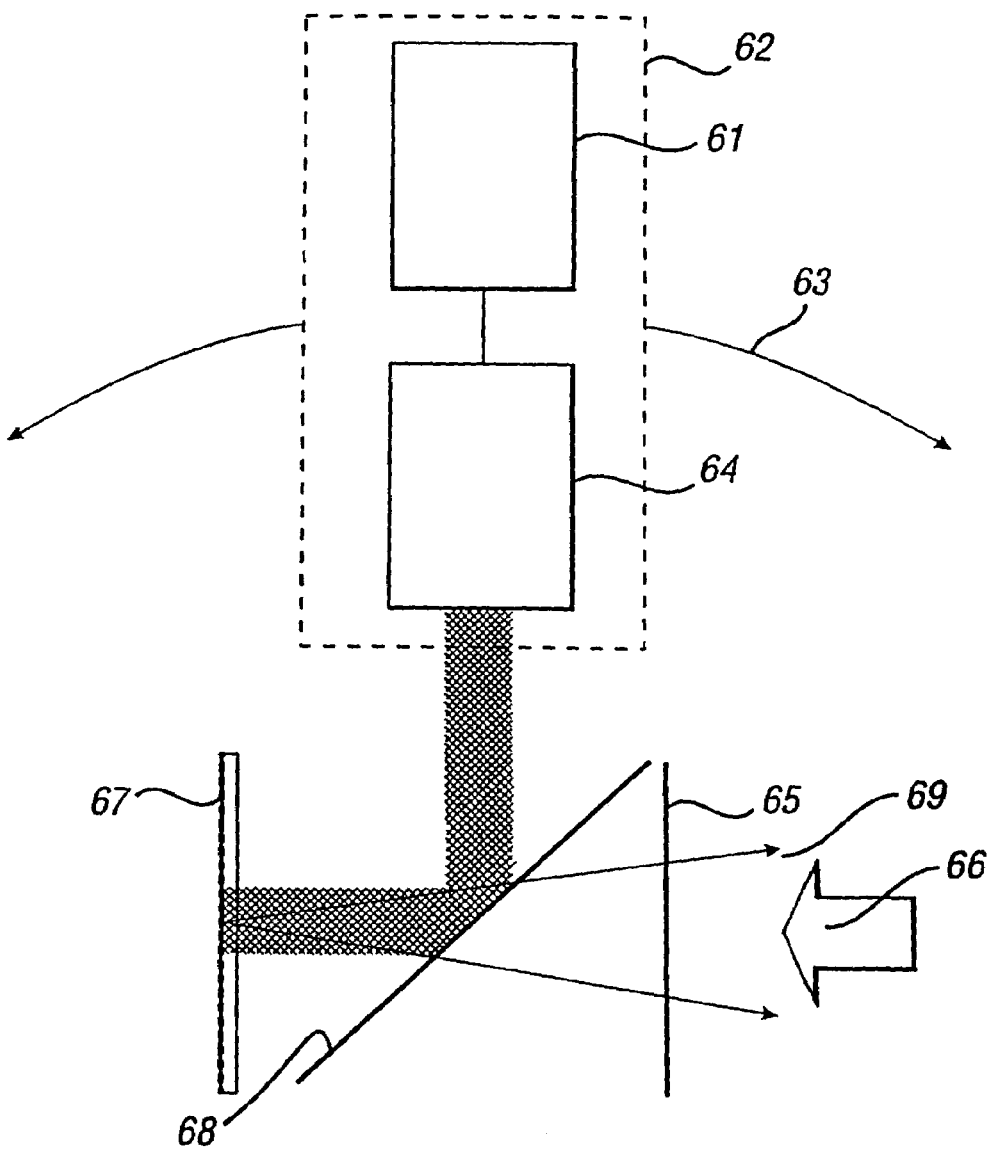
FIG. 6 shows schematically the layout used to measure fluorescences according to one example of the invention.

An arrangement as shown in FIG. 6 captures the whole luminescence, e.g. fluorescence, image of the entire platform at one shot without the need of any moving parts during measurement. Such a non-scanning device can be very simple and cheap and is especially suited for point-of-care application or portable systems. Another typical arrangement confines the coherent laser light down to micrometer dimensions by means of optical elements thereby increasing the electrical field in the focal point and scans the sensing area or areas.

It will be appreciated that a wide variety of samples can be analysed using the present technique. The sample is generally taken to be the entire solution to be analysed and this may comprise one or many substances to be detected. The sample may be a solution of purified and processed tissue, or other materials obtained from biopsy and examination investigation research and development including sample for diagnostic purposes. The sample may also be a biological medium, such as egg yolk, body fluids or components thereof, such as blood, serum and urine. It may also be surface water, solution or extracts from natural or synthetic media, such as soils or parts of plants, liquors from biological processes or synthetic liquors.

Figure 4A:
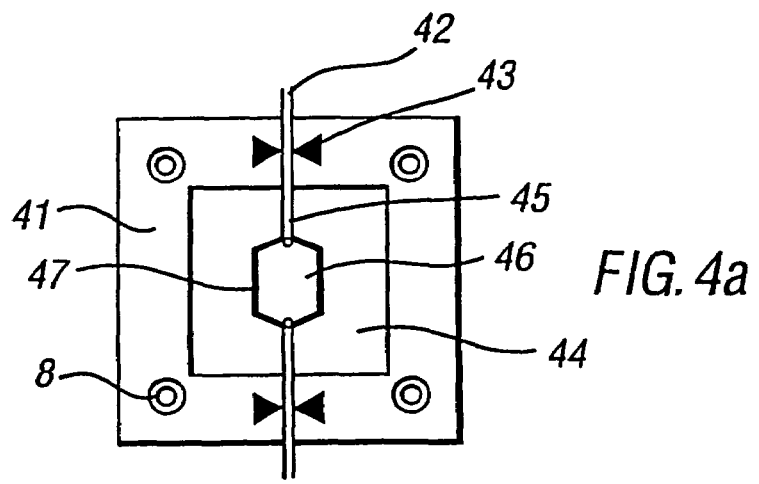
FIGS. 4a and 4b are schematic views showing a chip cartridge.
Figure 4B:
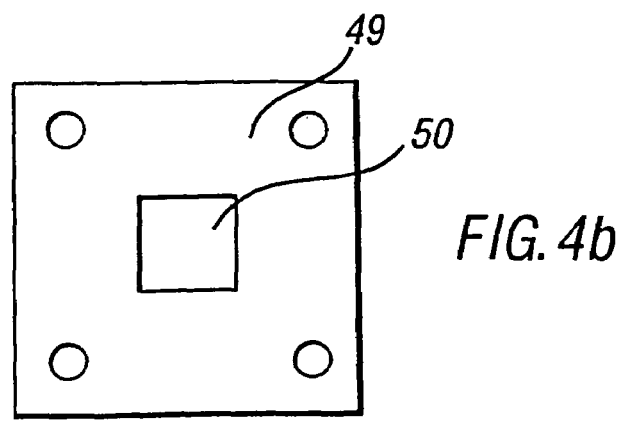

In order to carry out the measurement, the sample may be introduced into a sample cell of the type shown in FIGS. 4a and 4b of the drawings. This cell comprises a housing (41) which is made from a polymer such as PMMA. This polymer has been machined to define a central compartment (44) with dimensions corresponding to the dimensions of the platform. A further depression is formed in the compartment (44) to define a chamber (46) which is sealed around its edge by an O-ring (47). The chamber (46) is open at its top and bottom. Solution to be analysed can be introduced into the chamber (46) within the O-ring (47) through a flow line (45).

Flow within the flow line (45) can be controlled by a valves (43). The cell includes a cover (49) which can be located over and secured to housing (41) to close the top of the cell. The cover (49) includes a window (50) which locates over the compartment (46) and thereby allows radiation to pass through the cover and into the cell (46).

In use of the cell, the housing (41) is located against the surface of the platform which has the capture elements formed thereon so that the lid (49) is remote from that surface. This brings the compartment (46) into communication with the sensing area of the platform. The sample to be investigated is then fed into the compartment (46) through the flow line (45) so that it is brought into contact with the capture elements on the surface of the platform. A measurement of the fluorescence induced at various capture points is then carried out as previously described.

FIG. 8 illustrates possible alternative forms of the platform.

The sensing elements can be arranged in various ways, for instance rectangular, circular, hexagonal-centric, elipsoidal, linear or labyrinthine. The sensing area may be rectangular, round or of any other shape. The grooves may be arranged either equidistant linear or equidistant circular, or may correspond to segments of such structures.

The platform can be either rectangular or disc-shaped, or of any other geometry. The platform can comprise one or multiple sensing areas, each sensing area can comprise one or multiple capture elements, and each capture element can comprise one or multiple labelled or unlabelled capture molecules.

The platform can also be adapted to microtiter-type plates/devices in order to perform one or multiple assays in the individual microtiter wells. This can be achieved for all plate types: 96, 384, 1536, or higher numbers of wells, independently of the dimensions of the respective microtiter-plate.

The following is a specific example of a platform:

1. Physical Performance of 3-D Platform: Abnormal Reflection

1a. Platform 1

The gene chip transducer platform comprises a planar, transparent substrate (glass AF45 by Schott) of 0.7 mm thickness. Into the substrate a periodic surface structure is etched by photolithographical means (deposition of photoresist, <1 μm; writing of periodic structure into resist either by two beam interferometry/holography; etching the resist with reactive ion etching using Ar gas; stripping of residual photoresist).

The shapes of the surface structure are close to sinusoidal. The width (period) of a single structure is 360 nm. The depth of the grooves are approximately 38 nm.

On top of the homogeneously structured glass surface a dielectric transparent metal oxide film ($Ta_2O_5$) with high refractive index of app. 2.2 at 633 nm wavelength is deposited. The process is by ion plating. The layer thickness is 130 nm. The primary structure/architecture of the glass surface is transferred to the top of the metal oxide layer due to the highly energetic and anisotropic deposition process.

When a highly parallel, expanded, coherent laser beam is directed onto the transducer at distinct angles θ, corresponding to a so-called resonance position, almost all light is reflected by the transducer platform and the 0. order transmission intensity is reduced to less than 1% (compared to 90–95% at an arbitrary angle).

The width Δθ of the resonance condition, where almost all the light is reflected, is proportional to the wavelength λ (633 nm, fixed) and to the radiation loss coefficient α. The radiation loss coefficient is governed by the depth of the grating grooves, geometry and duty cycle of the corrugated structure, and increases almost quadratically with increasing groove depths. For our case (laser wavelength 633 nm, 130 nm metal oxide layer, 38 nm groove depth) the radiation loss is app. 2000/cm, i.e. the propagation distance of a guided laser beam in such a layer system before it is diffracted out of the platform by the periodic structure is 1/2000 cm, =5 μm. This is a surprisingly short distance. Therefore under these conditions no waveguiding occurs. By refinement of the platform specifications the propagation distance can be further reduced.

For characterization of the resonance effect, the intensity of the parallel beam (TE polarisation) is adjusted to 100 μW for a 4 mm diameter area (power meter Newport NRC 1835). The angle between platform normal and incident beam is rotated 1 to 2 degrees away from the centre position of the anomalous reflection (resonance condition). The centre position is at 2.5°. The platform is then rotated in steps of 5/1000° (Newport NRC controller PM 500) and the change of the power of the transmitted beam monitored. At resonance angle, less than 1% (<1 μW) of the original transmitted beam reaches the detector. The power of the incident laser beam is reflected totally (specularly reflected beam: approximately 100%).

The full width at half maximum of the resonance for abnormal reflection (FWHM) is in our case 0.9°. The homogeneity of the reflection over the whole transducer surface (18 mm×18 mm) is better than 90%.

1b. Platform 2

The shapes of the surface structure are close to rectangular. The width (period) of a single structure is 360 nm. The depth of the grooves are approximately 52 nm. On top of the homogenously structured glass surface a dielectric transparent metal oxide film (Ta205) with high refractive index of approximately 2.15 at 633 nm wavelength is deposited. The process is by sputtering. The layer thickness is 150 nm. The primary structure/architecture of the glass surface is transferred to the top of the metal oxide layer due to the highly energetic and anisotropic deposition process.

When a highly parallel, expanded, coherent laser beam is directed onto the transducer at distinct angles θ corresponding to a resonance position, almost all light is reflected by the transducer platform and the 0. order transmission intensity is reduced to less than 1% (compared to 90–95% at an arbitrary angle).

The width Δθ of the resonance condition, where almost all the light is reflected, is proportional to the radiation loss coefficient α. The radiation loss coefficient for our case (laser wavelength 633 nm, 150 nm metal oxide layer, 52 nm groove depth) is above 2000/cm, i.e. the propagation distance of light launched into such a layer system before it is diffracted out of the platform by the periodic structure is 1/2000 cm, =5 μm. Therefore under these conditions no waveguiding occurs.

For the characterization of the resonance effect, the intensity of the parallel beam (IE polarisation) is adjusted to 600 μW for a 4 mm diameter area (power meter Newport NRC 1835). The angle between platform normal and incident beam is rotated 4 degrees away from normal incidence. The platform is then rotated in steps of 5/1000° (Newport NRC controller PM 500) and the change of the power of the transmitted beam monitored. At resonance angle, less than 0.5% (<3 μW) of the original transmitted beam reaches the detector. The power of the incident laser beam is reflected totally (specularly reflected beam approximately 100%).

Due to the widening of the resonance width of platform 2 according to deeper grooves compared to platform 1 the resonance curves of the +1 and −1 diffraction order overlap creating a single extremely wide resonance located exactly at normal incidence. The full width at half maximum of the resonance for abnormal reflection (FW is in our case 4.2°. The homogeneity of the reflection over the whole transducer surface (18 mm×18 mm) is better than 95%.

2. Example for Gene Expression Analysis a) Preparation

Sensor platforms (dimensions 18×18 mm$^2$) of the type described with reference to FIG. 2 were first sonicated twice in chloroform (FLUKA, "purriss.") and subsequently twice in isopropanol (Merck, "Uvasol"), each for 15 min. The platform were then dried in vacuum and cleaned in a UV cleaner for 30 min (Boeckel industries Inc, model 135500). O-xylene was heated to 75° C. (stirring) and 2% v/v 3-glycidoxypropyl trimethoxysilane (Fluka, "purum") as well as 0.2% v/v N-ethyldiisopropylamine (Fluka, "purum") were added to the heated solvent (stirring). The platforms were mounted into racks and then incubated for 7 h in the solution at 75° C. (stirring). Subsequently, the platforms were sonicated three times in fresh acetonitrile (Fluka, "HPLC grade"), each for 15 min. The platforms were then sonicated in a solution of 2% v/v 3-amino-1-propanol (Fluka, "purum") in acetonitrile for 15 min and then incubated in the same solution over night at room temperature (stirring). Next day, the platforms were first sonicated three times for 15 min in fresh isopropanol (Fluka, "HPLC grade") and then three times for 15 min in fresh methanol (Merck, "Uvasol"). Finally, the platforms were dried and stored in vacuum.

b) Immobilization of Recognition Elements

Figure 5:
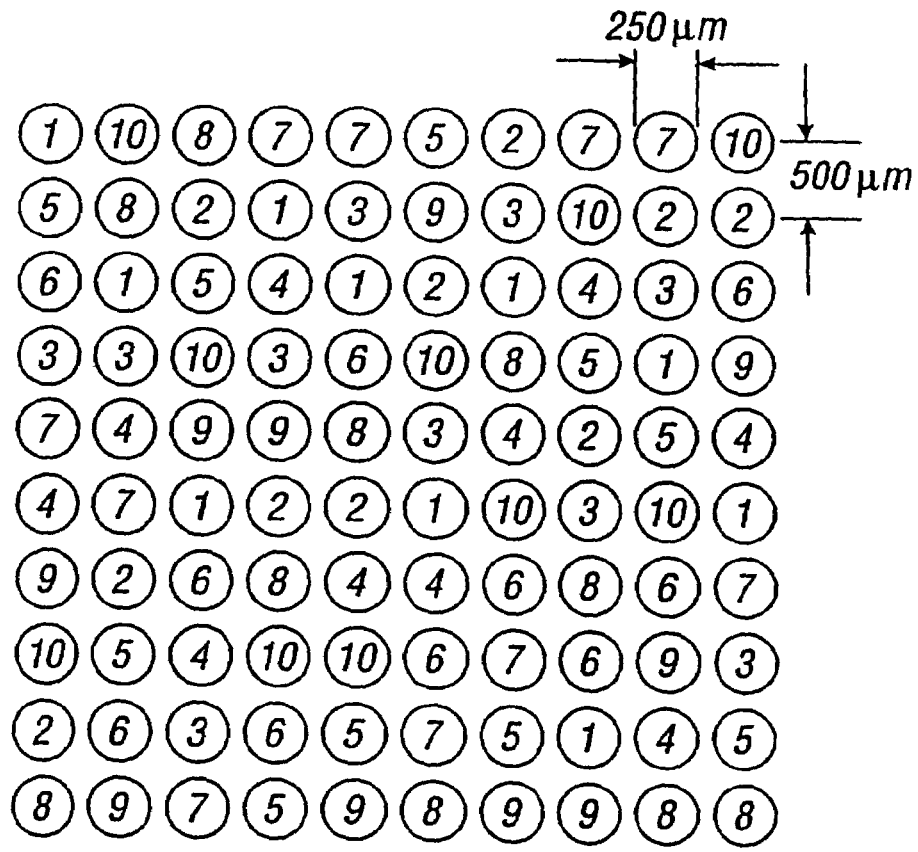
FIG. 5 shows an array layout in one example of the present invention.

Arrays consisting of 10 different cDNAs (each cDNA 10 replicates: CYP 450 1A1, CYP 450 2B1 EST., CYP 450 2B1, CYP 450 2B2, CYP 450 3A1 human, CYP 450 3A2, CYP 450 4A1, β-actin, GAPDH, external standard) were printed on the platforms with an ink-jet printer (Microdrop GmbH, Norderstedt, Germany). The concentration of the cDNA solutions was 50 ng/μL. The diameter (10 ink-jet droplets/position) was about 250 μm and pitch of the spots was about 500 μm. Therefore, the overall dimension of the 10×10 arrays was about 5×5 mm$^2$, The layout and assignment of the immobilized cDNA spots is schematically shown in FIG. 5. The arrays were printed in the centre of the platforms with the dimensions (18×18 mm$^2$). Subsequently, the platforms were incubated over night in a closed container in saturated water vapor atmosphere. Next day, the incubated chips can be baked for a defined period, say 1 minute at 80° C. Then the platforms were flushed with deionized water and dried with nitrogen flow.

c) Detection Set-Up

The detection set-up used is shown schematically in FIG. 6. An excitation laser (61) (HeNe laser, 633 nm, 1.3 mW) and a 20× beam expander (64) were jointly mounted (62) onto a goniometer (63). The expanded laser beam was directed towards the platform (67) by means of a dichroic mirror (68). The center of rotation for the laser beam lay in the plane of the metal oxide layer of the platform (67). The fluorescence emitted from the platform surface was collected via the dichroic mirror (68). Additional fluorescence filters (65) were used to separate fluorescence (69) from excitation light. A cooled CCD (Astrocam EEV 30/11) camera (66) equipped with a Nikon Noct lens Numerical Aperture 1.2) was used to measure fluorescence images from the surface platforms. The goniometer allowed the adjustment of the angle of the incident expanded laser beam with respect to the surface normal of the platform. Fluorescence images were taken under evanescent resonance conditions (i.e. the incident expanded laser beam was adjusted to that angle where the light transmitted through the platform shows a minimum).

d) Chip Cartridge

The platform were mounted to the specially designed cartridge (41) made from PMMA/polymer which is schematically shown in FIG. 4. The depression (44) had dimensions (18×18×0.7 mm$^3$) and the incubation chamber (46) was 0.2 mm deep. The solution in the incubation chamber was exchanged via flow channels (45) of 0.5 mm diameter that were drilled into the PMMA. The content of the cartridge was be exchanged via the inlet/outlet (42). The platform was positioned in the corresponding depression of the cartridge with the sensing area directed towards the incubation chamber. The cover (49) was fixed to press the platform against the sealing. The milled/micromachined window (50) in the cover allowed illumination with excitation light and the acquisition of fluorescence images of the platform surface. The valve-to-valve-volume of the cartridge was about 14 μL.

e) Denaturation Unit

A thermoelectric element was used to control the temperature for denaturation (79° C.), incubation, (42° C.) regeneration (79° C.) and wash (42° C.) of the platform in the flow cartridge.

f) Sample Preparation 2 groups of rats (each 3 rats) were used for the present study. One group (treated) was treated with 80 mg phenobarbital, sodium salt, in saline (0.9% w/v NaCl) per kg body weight and the second group (control) only with 0.9% NaCl. One daily treatment on 4 consecutive days was given. At the end of the 4 days, the animals were sacrificed and liver samples were snap frozen in liquid nitrogen and stored at −80° C.

Subsequently, the total RNA/mRNA was isolated and labeled by reverse transcription into first strand cDNA (incorporation of labeled deoxynucleotides, same or different fluorophore labels for control and treated), purified and dissolved in 20 μL hybridization buffer.

g) Assay Processing

A Cavro stepper syringe was used to pump/aspirate buffers and solutions into the cartridge. The following steps were executed to measure the CYP 450 induction in rat:

1) 30 min pre-wash at 79° C. with 1 ml hybridization buffer (HB), measurement of background 1 of the platform in contact with HB.
2) Injection of "control" sample into cartridge, 30 min denaturation at 79° C., then over night incubation at 42° C.
3) 10 min post-wash at 42° C. with 1 mL HB, measurement of "control" intensities of platform in contact with HB.
4) Regeneration: 30 min wash at 79° C. with 1 mL hybridization buffer (HB), measurement of background 2 of the platform in contact with HB.
5) Injection of "treated" sample into cartridge, 30 min denaturation at 79° C., then over night incubation at 42° C.
6) 10 min post-wash at 42° C. with 1 mL HB, measurement of "treated" intensities of platform in contact with HB.

All fluorescence images were measured under evanescent resonance conditions.

h) Data Processing

The net intensities (control-background 1 and treated-background2) of all spots were calculated and all intensities of the treated data set were normalized by the help of the intensities of the external standard. The expression ratios (fold change) between the respective genes were calculated by division of fold change=normalized treated/control.

Mean values of the each 10 replicates were calculated.

i) Results

ER-Chips measured under evanescent resonance conditions showed in general about 100 fold stronger intensities and improved signal/background ratios.

The mean values for fold change are summarized in the following table:

| GENE | Fold change |
| --- | --- |
| CYP 450 1A1 (rat) | 1.6 |
| CYP 450 2B1 EST. (rat) | 16 |
| CYP 450 2B1 (rat) | 25 |
| CYP 450 2B2 (rat) | 32 |
| CYP 450 3A1 (human) | 3.2 |
| CYP 450 3A2 (rat) | 2.5 |
| CYP 450 4A1 (rat) | 1.6 |
| β-actin (rat) | 2.1 |
| GAPDH (rat) | 2.3 |

3. Example to Illustrate Enhanced Amplification

Figure 7A:
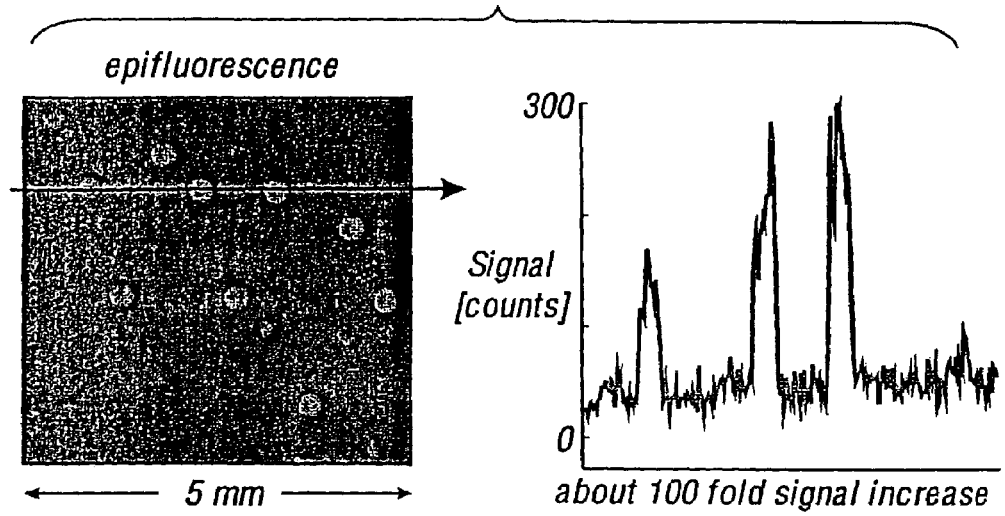
FIG. 7 shows a comparison of results obtained by a prior art technique and the present invention.
Figure 7B:
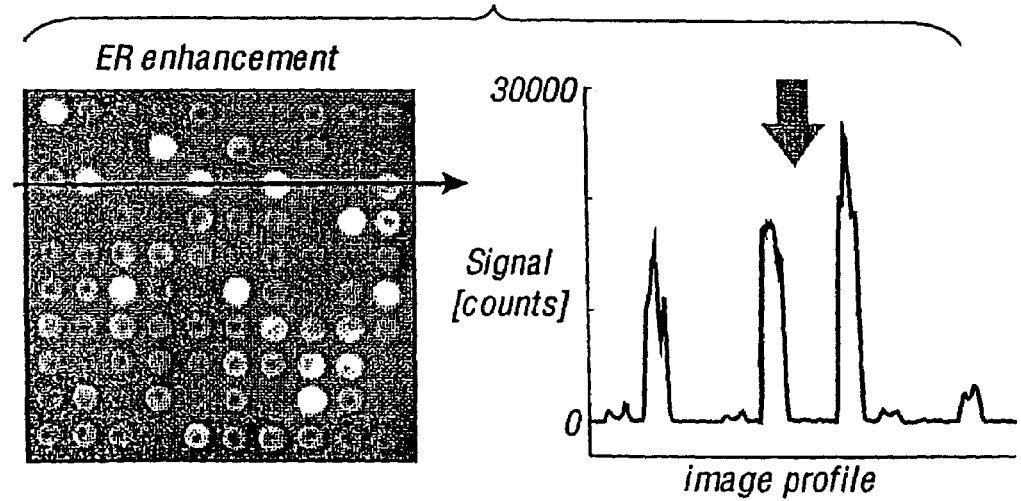
Figure 8A:
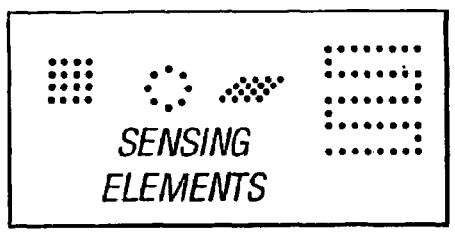
FIG. 8 illustrates alternative forms of platform.
Figure 8B:
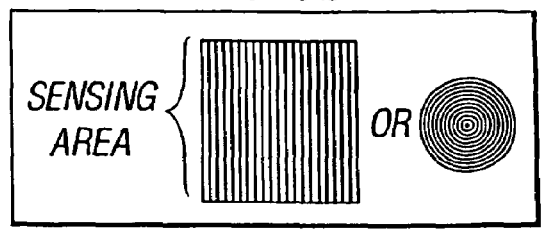
Figure 8C:
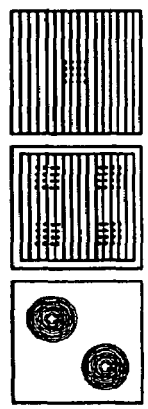
Figure 8D:
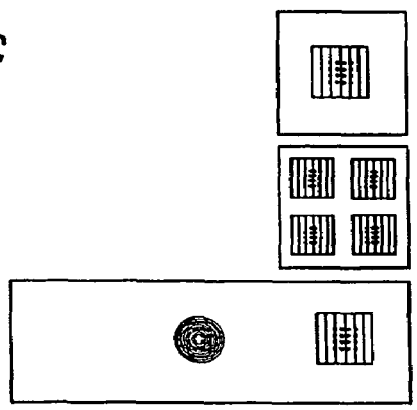
Figure 8E:
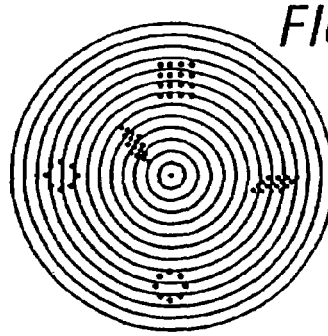
Figure 8F:
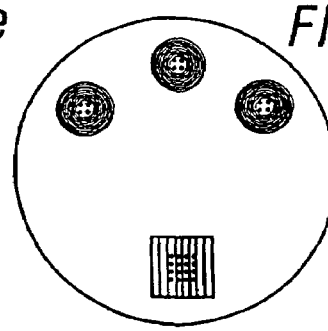
Figure 8G:
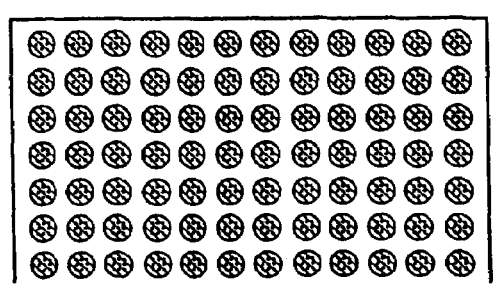

A platform was prepared and processed according to the example just described. Subsequent to the incubation with sample, 2 images were taken with the CDD camera detection set-up described above with reference to FIG. 6. The first image was taken in epifluorescence mode without adjustment to conditions for evanescent resonance ("epifluorescence" in FIG. 7a). The second image was taken under evanescent resonance conditions ("ER enhancement" in FIG. 7b), i.e. the angle of the incident laser beam was adjusted with respect to the surface normal until the light transmitted through the chip showed a minimum. The image profiles (net signals) show that intensities measured with ER-enhancement are about 100 fold stronger then the intensities obtained with conventional epifluorescence.

In the example described above a single sample cell (41) is used to bring the sample into contact with the sensing area of the platform. It will be appreciated that microtiter type sample container can be used in compensation with a platform having a plurality of sensing areas to allow measurement of a plurality of samples and thereby improve measurement efficiency.

4. Oligonucleotide Microchip for Discrimination of Single Nucleotide Polymorphism (SNP)

a. Chip Preparation

Sensor platforms (dimensions 18×18 mm2) of the type described with reference to FIG. 2 were first sonicated twice in chloroform (FLUKA, "purum.") and subsequently twice in isopropanol (Merck, "Uvasol"), each 15 min. The platforms were then dried in vacuum and cleaned in a UV cleaner for 30 min (Boeckel Industries Inc, model 135500). O-xylene was heated to 75° C. (stirring) and 2% v/v 3-glycidoxypropyl-trimethoxysilane (Fluka, "purum") as well as 0.2% v/v N-ethyldiisopropylamine (Fluka, "purum") were added to the heated solvent (stirring). The platforms were then mounted into racks and then incubated for 7 h in the solution at 75° C. (stirring). Subsequently, the platforms were washed three times with fresh acetonitrile (Fluka, "HPLC grade"), each for 15 min. Finally the platforms were dried and stored under vacuum.

b. Immobilization of Capture Elements

Two different amino-modified oligonucleotides (capture probes) were printed in a checkerboard-like layout (5×5=25 spots) onto the silanized platforms. A GMS 417 ring-pin arrayer was used for the printing (Genetic Microsystems, Boston, Mass.). The concentration of the oligonucleotides used as capture molecules was 100 nmol/ml. Diameter of the spots was 125 micrometer with 500 micrometer centre-to-centre distance. The 2 oligonucleotides were called cPM ("capture perfect match") and cMM ("capture mismatch") and differ only in one base:

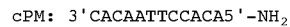

cPM: 3'CACAATTCCACA5'-NH$_2$

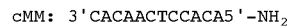

cMM: 3'CACAACTCCACA5'-NH$_2$ cPM and cMM were labeled with an amino group at the 5' end which enables covalent binding of the oligonucleotides to the epoxy-functionalized platforms. The arrays were printed in the centre of the platforms with the dimensions (18×18 mm2). Subsequently the platforms were incubated over night in a closed container in saturated water vapour atmosphere. Next day the chips were dried and the washed with 1 ml of aqueous 50% urea solution. Alternatively, an aqueous bovine serum albumine solution (BSA, 1 mg/ml) was used. After blocking the chips were flushed with deionized water and then dried with nitrogen flow.

c. Detection Set-Up

The CCD set-up described in the previous example was used.

d. Chip Cartridge

The cartridge described in the previous example was used.

e. Analytes/Samples

Two Cy-5-labeled oligonucleotides called PM ("perfect match") and MM ("mismatch") with sequences complimentary to the immobilized capture oligonucleotides cPM and cMM were used as the analytes:

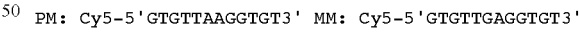

PM: Cy5-5'GTGTTAAGGTGT3'  MM: Cy5-5'GTGTTGAGGTGT3'

The concentration of the analyte solutions was 30 pM each.

f. Assay Processing

Figure 9C:
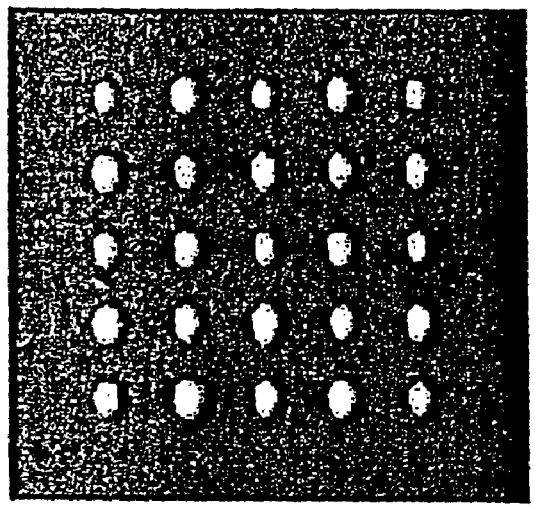
FIGS. 9a to 9c show fluorescence images obtained after incubation of 30 pm PM analyte, regeneration, and 30 pM MM analyte using the present platform under resonance conditions as described in Example 5.
Figure 9B:
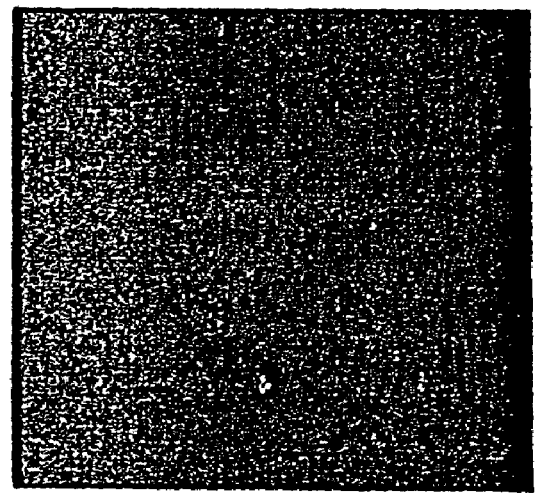
Figure 9A:
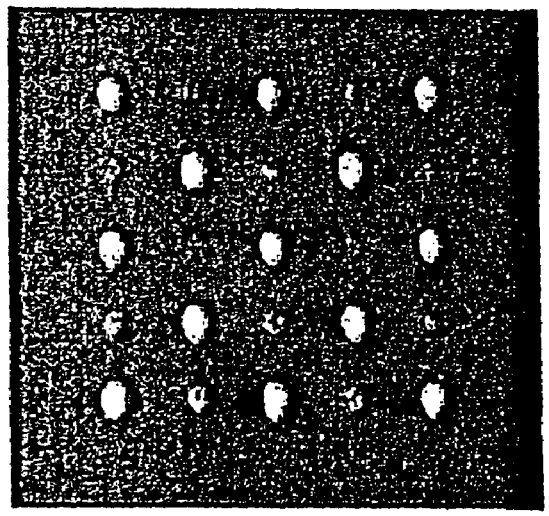

A platform was first washed 2 times with 1 ml of hybridization buffer (HB), with 1 min delay between the washings. Subsequently about 15 microliter PM analyte solution (30 pM) was injected into the flow cartridge. After 30 min of incubation, the platform was washed with 1 ml of HB and a fluorescence image ("PM" in FIG. 9a) was taken in the resonance position of the chip. Subsequently, the bound fluorescence labeled oligonucleotides were removed (stripped) by injection of 2×1 ml of an aqueous 50% urea solution with 2 min of delay between the injections. After additional 2 min the chip was washed by injection of 2×1 ml HB with 2 min delay between the injections and a fluorescence image ("regeneration" in FIG. 9b) was taken in the resonance position of the chip. Finally, approximately 15 microliter MM analyte solution (30 pM) was injected into the flow cartridge. After 30 min of incubation, the platform was again washed with 1 ml of BB and a fluorescence image ("MM" in FIG. 9c) was taken in the resonance position of the chip. All steps were performed at room temperature.

g. Data Processing

The mean intensity of the 2 different groups of capture spots (cPM and cMM) was calculated for both experiments (incubation of 30 pM PM analyte and 30 pM MM analyte). In addition, the difference of the mean intensity cPM-cMM and the ratio cPM/cMM was calculated.

h. Results

All data calculated were summarized in the following Table. The two oligonucleotide analytes, Cy-5 labelled PM and Cy-5 labelled MM, which differ only in one base (SNP) can be clearly distinguished from the obtained data.

|  | 30 pM PM analyte mean intensity [counts] | 30 pM MM analyte mean intensity [counts] |
|---|---|---|
| cPM spots | 1140 | 704 |
| cMM spots | 24 | 2075 |
| cPM-cMM | 1116 | −1371 |
| cPM/cMM | 48 | 0.34 |

5. Example for Antibody Immuno Assay

Primary antibodies are spatially resolved immobilized (for instance checkerboard pattern) on the surface of the sensor platform. The binding of the antigens to be detected and of the luminescence-labeled secondary antibodies (used for the detection of a second epitope of the individual antigens to be detected) is achieved by subsequent incubation, first with the analyte containing the various antigens in different concentrations, and then with the luminescence-labeled secondary antibodies.

Alternatively, the antigenes (analyte) and luminescence-labeled secondary antibodies can be mixed in a pre-incubation step, which allows complexation of luminescence-labeled secondary antibodies with the antigenes. After this pre-incubation step, the sensor platform surface is incubated with the mixture.

The luminescence labeled immuno complexes bound to the surface were quantified with the ER-set-up. (Pre-wash with suitable buffer, PBS, and post-wash if required).

6. Protein—Microchips for Multiplexed Immuno Assays a. Chip Preparation

Sensor platforms (dimensions 18×18 mm2) of the type described above were sonicated twice in chlororform (FLUKA, "purriss.") and subsequently twice in isopropanol (Merck, "Uvasol"), each 15 min. The platforms were dried in vacuum and cleaned in a UV cleaner for 30 min (Boeckel Industries Inc, model 135500). The chips were placed in a small container and stored in a 0.5 mMolar solution of octadecylphosphate in propanol for 24 hours. Subsequently, the chips were washed with 5 ml isopropanol in order to remove excess alkylphospate and dried in a nitrogen flow. This procedure created a Self-Assembled-Monolayer (SAM) of alkyphosphate at the surface of the platforms. This adhesion promoting layer rendered the platform hydrophobic (contact angle about 100°) and enabled the adsorption of proteins on the platform by hydrophobic interaction.

b. Immobilization of Capture Elements

Two different monoclonal antibodies, anti-human Chorinonic Gonadotropin (anti-hCG) and anti-Interleukin 6 (anti-IL6) were printed in a checkerboard-like layout onto the hydrophobic platforms in saturated water vapour atmosphere (4×4 array, 8 spots for each antibody). The concentration of the capture antibody solutions was 400 and 100 microgramm/ml respectively. An inkjet-printer was used for the printing (Microdrop, Norderstedt, Germany). The diameter of the spots was 150 micrometer with 320 micrometer centre-to-centre distance. The printed arrays were incubated for 2 hours in a closed container in saturated water vapour atmosphere. Subsequently, the chips were dried and flushed with 10 ml phosphate buffered saline (PBS) solution containing 10% bovine serum albumin (BSA), 5% sucrose and 0.02% sodium azide. This washing step blocked the hydrophobic surface of the chips by adsorption of BSA and rendered the surface more hydrophilic after the capture elements had been immobilized. As a consequence, the blocking procedure prevented non-specific binding of proteins to the platform which could cause increased background fluorescence. After blocking, the chips were flushed with deionized water and dried with nitrogen flow. The platforms were stored in a refrigerator until use.

c. Detection Set-Up

The CCD set-up described in Example 2 was used.

d. Chip Cartridge

The cartridge described in Example 2 was used.

e. Analytes/Samples 3 analyte solutions were prepared:
I) a solution containing 500 ng/ml Cy-5 labelled IL6, antigene
II) a solution containing 50 ng/ml Cy-5 labelled human Chorionic Gonadotropin (hCG), antigene
III) a preincubated mixture (1 hour) containing 50 ng/ml IL6 and 100 ng/ml polyclonal anti-IL6 antibody labelled with Cy5.

PBS pH 7.0 containing 1% BSA is used as solvent for the analytes.

f. Assay Processing

Three platforms (as described under 6b.) were prepared for the analyte incubation (cf. e.) by mounting the platforms into cartridges and washing with 1 ml of PBS pH 7.0 containing 1% BSA. Subsequently, about 15 microliter of the analyte solutions I), II) and III) were injected into the flow cartridges. The incubation time was 2 hours each for I) and II). For analyte III) the incubation time was 12 hours. After incubation of the analyte, the platforms were washed with 1 ml of PBS pH 7.0 containing 1% BSA. Fluorescence images were taken from the chips under off-resonance conditions (epi fluorescence, about 7° apart from resonance angle) and under resonance condition for each chip (resonance, incident light about 2.5° with respect to normal). Images and data obtained are shown in FIG. 10. All steps were performed at room temperature.

g. Data Processing

The mean intensities and the background of the spots were calculated by help of Imagene Array software (Biodiscovery, Los Angeles, Calif.). Spot mean in FIG. 10 represents the background corrected mean intensity of the respective capture elements under interest. In addition, the noise was calculated as standard deviation of the background from the fluorescence images. Therefore, signal/noise in FIG. 10 corresponds the ratio of spot mean over background standard deviation.

h. Results

All data calculated are summarized in FIG. 10. Images and data obtained in epifluorescence mode as well as under resonance conditions are summarised in FIG. 10. Rows I) and II) show the results of an immunoreaction between immobilized monoclonal capture antibodies and labeled antigenes (Cy5-labelled IL6 and hCG respectively). Row III) corresponds to a sandwich type immuno reaction between an immobilized monoclonal antibody (anti-IL6) and a preincubated mixture of IL6 antigene and a CY5-labelled secondary polyclonal antibody against IL6.

For the results of row I) the signal intensity increases from 46 counts in epi fluorescence mode to 1100 counts in resonance mode of the platform. This corresponds to an enhancement factor of about 24 regarding the spot mean values. The signal/noise ratio improves from 7.0 (epi fluorescence) to 69.2 (resonance), corresponding to a factor of 10.

For the results of row II) the signal intensity increases from 32 counts in epi fluorescence mode to 646 counts in resonance mode of the platform. This corresponds to an enhancent factor of about 20 regarding the spot mean values. The signal/noise ratio improves from 5.0 (epi fluorescence) to 75.1 (resonance), corresponding to a factor of 15.

For the results of row III) the signal intensity increases from 25 counts in epi fluorescence mode to 296 counts in resonance mode of the platform. This corresponds to an enhancent factor of about 12 regarding the spot mean values. The signal/noise ratio improves from 3.8 (epi fluorescence) to 44.1 (resonance), corresponding to a factor of 12.

Spot mean and signal/noise values for all 3 assays are at least one order of magnitude higher for the chips in resonance mode compared to the same chips in non-resonance mode (epi fluorescence). The fluorescence images of rows I) and II) are complementary (checkerboard-layout). All chips used have the same set of capture elements, i.e. monclonal anti-hCG and monoclonal anti-IL6.

Examples 7a, 7b, 8 and 9 Describe the Additional Amplification Obtained when using TM Excitation and the Enhanced Signal Intensity when Directing the Incident Beam onto the Transparent Substrate Side of the Platform (Chip)

Physical properties of the platforms (Chips 1 to 6) used in Examples 7a, 7b, 8 and 9 are as follows. Groove depth means depth of corrugation layer. The high-refractive index layer is pure $Ta_2O_5$. The angles of the respective resonance positions are with respect to normal incidence 0°).

TE part: The laser beam is adjusted so that the expanded beam strikes chip 1 at normal incidence with the incident light polarised so as to provide TE excitation. The laser is rotated on a goniometer within the plane of the drawing until the angle of abnormal reflection is reached. The fluorescence signals of a variety of spots excited by the laser light are recorded by the CCD camera. This is repeated using chip 2.

TM part: the incident laser light is rotated by 90 degrees and the beam adjusted so that the expanded beam strikes chip 1 at normal incidence. This geometry creates TM excitation. The laser is rotated on a goniometer within the plane of the drawing until the angle of abnormal reflection is reached. The fluorescence signals of a variety of spots excited by the laser light are recorded by the CCD camera. This is repeated using chip 2.

Resulting peak intensities at the abnormal reflection angle are as follows:

TE/TM comparison: For chip 1 the maximum of the fluorescence signal for TE excitation reaches 2,750 counts, for TM almost 9,000 counts. For chip 2 the values are 10,000 vs. 40,000 counts respectively.

7b) Example with CCD Camera to Further Demonstrate Amplification by TM Excitation Using chip 3, the platform according to FIG. 6 is aligned so that the plane of polarization of the linearly polarized and expanded laser light is perpendicular to the longitudinal axis of the grooves of the corrugated surface, i.e. giving rise to TM excitation. Using this geometry and orientation, the fluorescence yield is even higher when compared to the arrangement where the plane of polarization is parallel to the grooves (TE excitation).

The angle of the light incident on the chip is varied between 0° (normal incidence) and 10° with respect to the surface normal. The maximum of the fluorescence intensity is found at 3.15°. Fluorecence images are taken by means of the CCD camera as a function of the angle of the light incident on the chip. The mean value of the fluorescence intensity of 32 selected spots is calculated and the mean background intensity is subtracted for every image.

Obtained fluorescence intensities, background values, and the relative change of the fluorescence as function of the angle of the incident light are summarized in the table below.

For the net fluorescence signal (signal minus background) we measure an enhancement of fluorescence yield by a factor of 223.

| Example | Groove depth | Thickness of $Ta_2O_5$ | Resonance angle TE | Resonance angle TM |
|---|---|---|---|---|
| 7a) chip 1 | 55 nm | 168 nm | 0.8° | 9° |
| 7a) chip 2 | 40 nm | 161 nm | 0.8° | 9° |
| 7b) chip 3 | 35 nm | 180 nm | 4.25° | 3.15° |
| 8) chip 4 | 35 nm | 150 nm | 2° | 7.7° |
| 9) chip 5 | 40 nm | 185 nm | 6.5° | 2.0° |
| 9) chip 6 | 55 nm | 190 nm | 6.0° | 2.6° |

7a) Comparison Between TE and TM Polarized Excitation Light for a CCD Set-Up with Dichroic Mirror.

The experimental set-up of FIG. 6 is used for each measurement. The hardware is the same for both parts of the experiments. The platform (chip) is oriented in a way that the grooves are perpendicular to the plane of drawing FIG. 6.

| Angle [°] | Signal (counts) | Background (counts) | Signal-background (counts) | Normalized signal |
|---|---|---|---|---|
| 0 | 28.7 | 23.6 | 5.1 | 1 |
| 1 | 30.4 | 22.9 | 7.5 | 1.5 |
| 2 | 36.3 | 24.1 | 12.2 | 2.4 |
| 3 | 203.8 | 26.4 | 177.4 | 34.8 |
| 3.1 | 723.9 | 29.0 | 694.9 | 136.3 |
| 3.125 | 979.6 | 29.7 | 949.9 | 186.3 |
| 3.15 | 1170.9 | 30.7 | 1140.2 | 223.6 |
| 3.175 | 1132.0 | 30.3 | 1101.7 | 216.0 |
| 3.2 | 955.9 | 31.9 | 924.0 | 181.2 |
| 3.225 | 523.8 | 27.1 | 496.7 | 97.5 |
| 3.5 | 73.7 | 29.4 | 44.3 | 8.7 |
| 4 | 40.5 | 26.5 | 14.0 | 2.8 |
| 7 | 30.4 | 25.3 | 5.1 | 1 |
| 10 | 30.0 | 23.8 | 6.2 | 1.2 |

Figure 11:
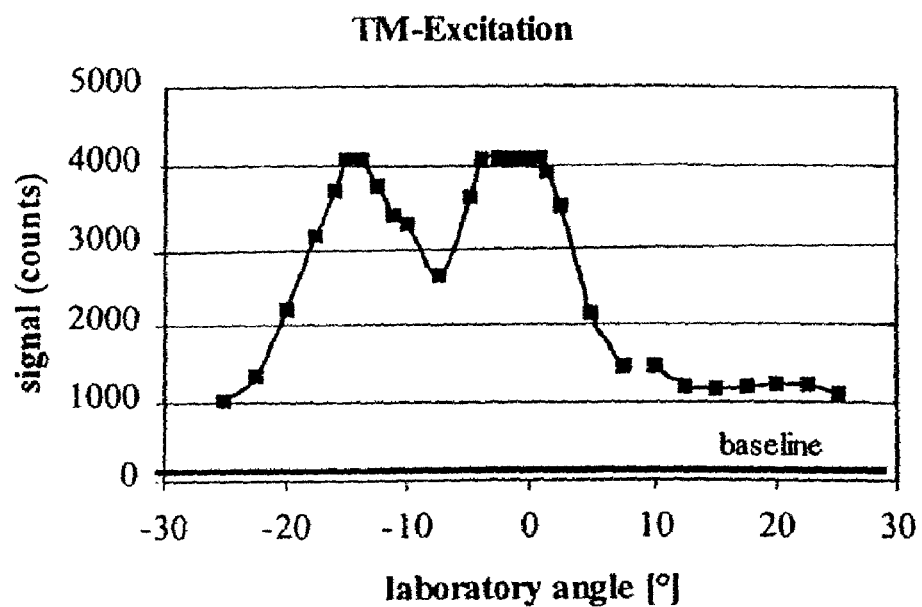
FIG. 11 shows angular distribution of fluorescence intensity with TM excitation.
Figure 12:
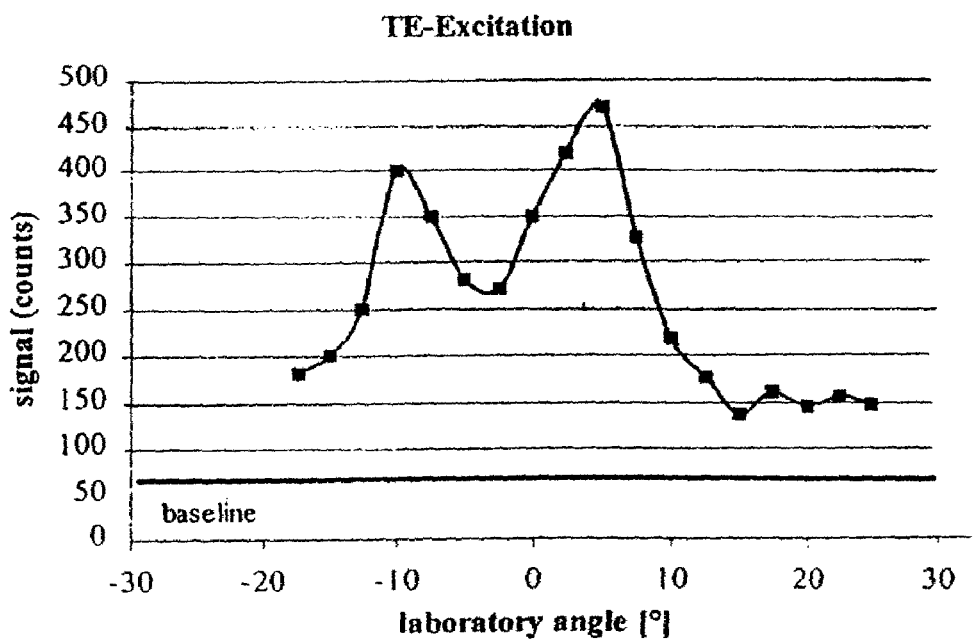
FIG. 12 shows angular distribution of fluorescence intensity with TE excitation.

8. Comparison between TE and TM Polarized Excitation Light for a CCD Set-Up with Dichroic Mirror The experimental set-up differs from that in Example 7: the detector is rotated in the horizontal plane around chip 4 which is excited at resonance position. The detector measures the fluorescence emitted into the whole solid angle. The results are illustrated in FIGS. 11 and 12.

With excitation of the TM configuration the measured fluorescence intensity exceeds the saturation level of 4096 (12 bit camera), whereas with TE configuration intensities are up to 400 counts. Baseline/background for both experiments is approx. 75 counts.

9. Example with Laser Scanner to Demonstrate Amplification by TE vs. TM Orientation, with Results on Incident Light onto the High Refractive Index Side Compared with Light Incident onto the Substrate Side A laser scanner (GSI Lumonics ScanArray 4000) is used to obtain the fluorescence images. The laser scanner focusses the excitation laser light (632.8 nm) to a diameter of 10 μm and a photomultiplier collects the fluorescence photons at a given position of the platform (hereafter: chip). A 2-dimensional image is created by scanning across the chip in 10 μm steps. The fluorescence intensities of each chip are measured at 4 different orientations:

9a) chips oriented with laser light incident from the corrugated high refractive index side (abbreviated CHRIS); polarisation parallel to longitudinal axis of grooves ("TE");

9b) chips oriented with laser light incident from the corrugated high refractive index side; polarisation perpendicular to longitudinal axis of grooves ("TM");

9c) chips oriented with laser light incident from substrate side; polarization parallel to longitudinal axis of grooves (TE);

9d) chips oriented with laser light incident from substrate side; polarization perpendicular to longitudinal axis of grooves (TM).

The two individual chips 5 and 6 are analyzed. The mean value of the fluorescence intensities of 8 selected spots is calculated for each chip and the results are given in the table below:

| Chip | Orientation of polarisation | Light incident from | Fluorescence signal (counts) | Normalized value |
|---|---|---|---|---|
| Chip 5 | parallel to grooves (TE) | CHRIS | 979 | 1 |
| Chip 5 | parallel to grooves (TE) | substrate | 7059 | 7.2 |
| Chip 5 | perpendicular to grooves (TM) | CHRIS | 6661 | 6.8 |
| Chip 5 | perpendicular to grooves (TM) | substrate | 42669 | 43.6 |
| Chip 6 | parallel to grooves (TE) | CHRIS | 1077 | 1 |
| Chip 6 | parallel to grooves (TE) | substrate | 5116 | 4.8 |
| Chip 6 | perpendicular to grooves (TM) | CHRIS | 7415 | 6.9 |
| Chip 6 | perpendicular to grooves (TM) | substrate | 52826 | 49.0 |

It will be appreciated that many alternatives to the described embodiments are possible. Thus different excitation geometries may be exploited depending on application area, requirements, costs, geometrical restrictions etc.

Another feature of the present platform is that it allows larger sets of data to be acquired in parallel. Also it can be used several times. Immobilised affinity complexes can be regenerated at elevated temperature using organic solvents and/or chaotropic reagents (salt solutions) while maintaining the binding capacity substantially completely.

In the description given above the whole area of a sensing region is irradiated. It is possible also to use a laser with a non-expanded focused beam and to scan the sensing area so that end capture element is excited in turn. This arrangement permits the use of a cheaper photodetector than the CCD camera e.g. a photomultiplier, or avalanche photodiode can be used. Also this arrangement will enhance further the sensitivity due to the fact that laser energy is more confined.

It is possible also to design platforms in accordance with the present invention for use as microscope slides thereby allowing them to be used with a fluorescence microscope.

The platforms can also be designed for use with large scale microfluidic systems such as that described in WO97/02357.

In the above description the use of the platform has been described in application which excite and sense fluorescence. It will be appreciated that the platform can be used in arrangements where affinity reactions are detected by changes of luminescence. It will be also appreciated that the platform can be used in arrangements where affinity reactions are detected by changes in refractive index.

Platforms in accordance with the present invention can be used in many applications of which the following is a non-exclusive list.

Gene expression
Genomics
Pharmacogenomics
Toxicogenomics
Toxicoproteomics
Genetics
Pharmacogenetics
Toxicogenetics
Exon/intron expression profiling
Human Leukocyte Antigens (HLA) typing
Analysis of splicing variants
Proteomics (on-chip protein assays)
Patient monitoring (drug, metabolites, and markers)
Point-of-care, "personalised medicine"
Diagnostics
on-chip 2d gels for proteomics or 2d separation in general
SNP (single nucleotides polymorphism), mini-sequencing
High Throughput Screening
Combinatorial chemistry
Protein-protein interaction
Molecular interaction
Chip-based protein-antibody and peptide interaction
Green fluorescent protein (GFP)
in-situ hybridisation
confocal microscopy
fluorescence correlation spectroscopy (FCS)
conventional microscopy
MALDI-TOF MS

What is claimed is:

1. Apparatus for analysing samples comprising a platform including an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define one or multiple sensing regions, said grooves being configured such that either a) coherent light incident on said platform is diffracted into individual beams or diffraction orders which interfere resulting in reduction of the transmitted beam and an abnormal high reflection of the incident light thereby generating an enhanced evanescent field at the surface of the one or multiple sensing regions; or b) coherent and linearly polarized light incident on said platform is diffracted into individual beams or diffraction orders which interfere resulting in almost total extinction of the transmitted beam and an abnormal high reflection of the incident light thereby generating an enhanced evanescent field at the surface of the one or multiple sensing regions, wherein the enhanced evanescent field interacts with luminescent material on or in the vicinity of one or more of the sensing regions so as to produce a detectable luminescent signal;

said apparatus further including means for generating a light beam and for directing the beam so that it is incident upon the platform on the side of the substrate that does not have the optically transparent layer disposed thereon at an angle which causes evanescent resonance to occur in at least one sensing region of the platform to thereby create an enhanced resonant field in the at least one sensing region of the platform and means for detecting a characteristic of an affinity reaction occurring on or in the vicinity of, or a characteristic of a material disposed on or in the vicinity of, the at least one sensing region of the platform.

2. Apparatus according to claim 1, wherein the light generating means comprises a laser for emitting a coherent laser beam.

3. Apparatus according to claim 2, wherein the means for directing the beam includes optical elements for directing the laser beam so that it is incident on the platform at an angle $\theta$, the angle $\theta$ being defined by the expression $\sin\theta = n - \lambda/\Lambda$ where $\Lambda$ is a period of the diffractive grooves, $\lambda$ is the wavelength of the light and n is the effective refractive index of the optically transparent layer.

4. Apparatus according to claim 2, wherein the light generating mean is adapted to generate light having a linear polarisation component which gives rise to TM excitation.

5. Apparatus according to claim 1, wherein the detecting means is arranged to detect luminescence such as fluorescence phosphorescence, chemi-luminescence, and electro-luminescence.

6. Apparatus according to claim 1 wherein the light generating mean is adapted to generate light having a linear polarisation component which gives rise to TM excitation.

7. Apparatus according to claim 1, wherein the light beam incident upon the platform has a polarization that is substantially perpendicular to the grooves in the at least one sensing region so as to give rise to TM excitation in the at least one sensing region.

8. Apparatus according to claim 1, wherein the light beam incident upon the platform has a polarization that is substantially parallel to the grooves in the at least one sensing region so as to give rise to TE excitation in the at least one sensing region.

9. Apparatus for analysing samples comprising a platform including an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define one or multiple sensing regions, said grooves being configured such that either a) coherent light incident on said platform is diffracted into individual beams or diffraction orders which interfere resulting in reduction of the transmitted beam and an abnormal high reflection of the incident light thereby generating an enhanced evanescent field at the surface of the one or multiple sensing regions; or b) coherent and linearly polarized light incident on said platform is diffracted into individual beams or diffraction orders which interfere resulting in almost total extinction of the transmitted beam and an abnormal high reflection of the incident light thereby generating an enhanced evanescent field at the surface of the one or multiple sensing regions, wherein the enhanced evanescent field interacts with luminescent material on or in the vicinity of one or more of the sensing regions so as to produce a detectable luminescent signal;

said apparatus further including means for generating a light beam and for directing the beam so that it is incident upon the platform on the side of the substrate having the optically transparent layer disposed thereon at an angle which causes evanescent resonance to occur in at least one sensing region of the platform to thereby create an enhanced resonant field in the at least one sensing region of the platform, and means for detecting a characteristic of an affinity reaction occurring on or in the vicinity of, or a characteristic of a material disposed on or in the vicinity of, the at least one sensing region of the platform, wherein the light generating means is adapted to generate light having a linear polarisation component which gives rise to TM excitation.

10. Apparatus according to claim 9, wherein the light generating means comprises a laser for emitting a coherent laser beam.

11. Apparatus for analysing samples comprising a platform including an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define one or multiple sensing regions, said grooves being configured such that either a) coherent light incident on said platform is diffracted into individual beams or diffraction orders which interfere resulting in reduction of the transmitted beam and an abnormal high reflection of the incident light thereby generating an enhanced evanescent field at the surface of the one or multiple sensing regions; or b) coherent and linearly polarized light incident on said platform is diffracted into individual beams or diffraction orders which interfere resulting in almost total extinction of the transmitted beam and an abnormal high reflection of the incident light thereby generating an enhanced evanescent field at the surface of the one or multiple sensing regions, wherein the enhanced evanescent field interacts with luminescent material on or in the vicinity of one or more of the sensing regions so as to produce a detectable luminescent signal;

said apparatus further including means for generating a light beam and for directing the beam so that it is incident upon the platform on the side of the substrate having the optically transparent layer disposed thereon at an angle which causes evanescent resonance to occur in at least one sensing region of the platform to thereby create an enhanced resonant field in the at least one sensing region of the platform, and means for detecting a characteristic of an affinity reaction occurring on or in the vicinity of, or a characteristic of a material disposed on or in the vicinity of, the at least one sensing region of the platform, wherein the light beam incident upon the platform has a polarization that is substantially perpendicular to the grooves in the at least one sensing region so as to give rise to TM excitation in the at least one sensing region.

12. Apparatus for analysing samples comprising a platform including an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define one or multiple sensing regions, said grooves being configured such that either a) coherent light incident on said platform is diffracted into individual beams or diffraction orders which interfere resulting in reduction of the transmitted beam and an abnormal high reflection of the incident light thereby generating an enhanced evanescent field at the surface of the one or multiple sensing regions; or b) coherent and linearly polarized light incident on said platform is diffracted into individual beams or diffraction orders which interfere resulting in almost total extinction of the transmitted beam and an abnormal high reflection of the incident light thereby generating an enhanced evanescent field at the surface of the one or multiple sensing regions, wherein the enhanced evanescent field interacts with luminescent material on or in the vicinity of one or more of the sensing regions so as to produce a detectable luminescent signal;

said apparatus further including means for generating a light beam and for directing the beam so that it is incident upon the platform on the side of the substrate having the optically transparent layer disposed thereon at an angle which causes evanescent resonance to occur in at least one sensing region of the platform to thereby create an enhanced resonant field in the at least one sensing region of the platform, and means for detecting a characteristic of an affinity reaction occurring on or in the vicinity of, or a characteristic of a material disposed on or in the vicinity of, the at least one sensing region of the platform, wherein the light beam incident upon the platform has a polarization that is substantially parallel to the grooves in the at least one sensing region so as to give rise to TE excitation in the at least one sensing region.

13. A platform for use in sample analysis comprising an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures, each comprising substantially parallel periodic grooves which define one or multiple sensing regions, said grooves being configured such that coherent and linearly polarized light incident on said platform is diffracted into individual beams or diffraction orders which interfere resulting in a substantially total extinction of the transmitted beam and an abnormal high reflection of the incident light thereby generating an enhanced evanescent field at the surface of the one or multiple sensing regions;

wherein the enhanced evanescent field interacts with luminescent material on or in the vicinity of one or more of the sensing regions so as to produce a luminescent signal, and wherein a light beam incident upon the platform having a polarization that is substantially perpendicular to the grooves in at least one sensing region gives rise to TM excitation in the at least one sensing region.

14. A platform for use in sample analysis comprising an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures, each comprising substantially parallel periodic grooves which define one or multiple sensing regions, said grooves being configured such that coherent and linearly polarized light incident on said platform is diffracted into individual beams or diffraction orders which interfere resulting in a substantially total extinction of the transmitted beam and an abnormal high reflection of the incident light thereby generating an enhanced evanescent field at the surface of the one or multiple sensing regions;

wherein the enhanced evanescent field interacts with luminescent material on or in the vicinity of one or more of the sensing regions so as to produce a luminescent signal, and wherein a light beam incident upon the platform having a polarization that is substantially parallel to the grooves in at least one sensing region gives rise to TE excitation in the at least one sensing region.

15. An apparatus including a platform for use in sample analysis, said platform having one or more sensing areas or regions, each for receiving a capture element or elements which when the platform is irradiated with coherent light can interact to provide an indication of an affinity reaction, wherein each capture element includes two or more types of capture molecule, said platform further comprising an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define the one or multiple sensing areas or regions, said grooves being so profiled, dimensioned and oriented that coherent light incident on said platform is diffracted into individual beams or diffraction orders which interfere resulting in reduction of the transmitted beam and an abnormal high reflection of the incident light thereby generating an enhanced evanescent field at a surface of the one or more sensing areas, wherein said light incident on the platform is incident on the side of the substrate that does not have the optically transparent layer formed thereon.

16. An apparatus including a platform for use in sample analysis, said platform having one or more sensing areas or regions, each for receiving a capture element or elements which when the platform is irradiated with coherent light can interact to provide an indication of an affinity reaction, wherein each capture element includes two or more types of capture molecule, said platform further comprising an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define the one or multiple sensing areas or regions, said grooves being so profiled, dimensioned and oriented that coherent and linearly polarised light incident on said platform is diffracted into individual beams or diffraction orders which interfere resulting in a substantially total extinction of the transmitted beam and an abnormal high reflection of the incident light thereby generating an enhanced evanescent field at a surface of the one or more sensing areas, wherein said light incident on the platform is incident on the side of the substrate that does not have the optically transparent layer formed thereon.

17. The apparatus of claim 1, 15 or 16, wherein the grooves of at least one of said corrugated structures are profiled, dimensioned and oriented such that the propagation distance of the incident light within the at least one corrugated structure is less than about 10 μm.

18. The apparatus of claim 1, 15 or 16, wherein the depth of the grooves is in the range of about 50 nm to the thickness of the optically transparent layer.

19. The apparatus of claim 1, 15 or 16, wherein the grooves of at least one of said corrugated structures are profiled, dimensioned and oriented such that the radiation loss coefficient of the incident light within the at least one corrugated structure is on the order of 2000/cm or greater.

20. The apparatus of claim 1, 15 or 16, wherein the depth of the grooves is in the range of about 50 nm to the thickness of the optically transparent layer.

21. The apparatus of claim 1, 15 or 16, wherein
the depth of the grooves is in the range of about 30 nm to the thickness of the optically transparent layer,
the thickness of the optically transparent layer is in the range of 30 to 1000 nm,
the period of the corrugated structure is in the range of 200 to 1000 nm,
the ratio of groove depth to the thickness of the optically transparent layer is in the range of 0.02 to 1, and
the ratio of grove width to the period of the grooves is in the range of 0.2 to 0.8.

22. A platform for use in sample analysis, said platform having one or more sensing areas or regions, each for receiving a capture element or elements which when the platform is irradiated with coherent light can interact to provide an indication of an affinity reaction, wherein each capture element includes two or more types of capture molecule, said platform further comprising an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define the one or multiple sensing areas or regions, said grooves being so profiled, dimensioned and oriented that coherent and linearly polarised light incident on said platform is diffracted into individual beams or diffraction orders which interfere resulting in a substantially total extinction of the transmitted beam and an abnormal high reflection of the incident light thereby generating an enhanced evanescent field at a surface of the one or more sensing areas, wherein the polarized light has a polarization that is substantially aligned with the orientation of the grooves in at least one of said sensing areas or regions.

23. A platform for use in sample analysis, said platform having one or more sensing areas or regions, each for receiving a capture element or elements which when the platform is irradiated with coherent light can interact to provide an indication of an affinity reaction, wherein each capture element includes two or more types of capture molecule, said platform further comprising an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define the one or multiple sensing areas or regions, said grooves being so profiled, dimensioned and oriented that coherent and linearly polarised light incident on said platform is diffracted into individual beams or diffraction orders which interfere resulting in a substantially total extinction of the transmitted beam and an abnormal high reflection of the incident light thereby generating an enhanced evanescent field at a surface of the one or more sensing areas, wherein the polarized light has a polarization that is substantially perpendicular to the orientation of the grooves in at least one of said sensing areas or regions.

24. A platform for use in sample analysis, said platform having one or more sensing areas or regions, each for receiving a capture element or elements which when the platform is irradiated with coherent light can interact to provide an indication of an affinity reaction, wherein each capture element includes two or more types of capture molecule, said platform further comprising an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define the one or multiple sensing areas or regions, said grooves being so profiled, dimensioned and oriented that coherent and linearly polarised light incident on said platform is diffracted into individual beams or diffraction orders which interfere resulting in a substantially total extinction of the transmitted beam and an abnormal high reflection of the incident light thereby generating an enhanced evanescent field at a surface of the one or more sensing areas, wherein the polarized light has a linear polarization component that gives rise to TM excitation in at least one of said sensing areas or regions.

25. A platform for use in sample analysis, said platform having one or more sensing areas or regions, each for receiving a capture element or elements which when the platform is irradiated with coherent light can interact to provide an indication of an affinity reaction, wherein each capture element includes two or more types of capture molecule, said platform further comprising an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define the one or multiple sensing areas or regions, said grooves being so profiled, dimensioned and oriented that coherent light incident on said platform is diffracted into individual beams or diffraction orders which interfere resulting in reduction of the transmitted beam and an abnormal high reflection of the incident light thereby generating an enhanced evanescent field at a surface of the one or more sensing areas,
the platform further including means for generating a light beam and for directing the beam so that it is incident upon the platform on the side of the substrate that does not have the optically transparent layer disposed thereon at an angle which causes evanescent resonance to occur in at least one sensing area of the platform to thereby create an enhanced resonant field in the at least one sensing area of the platform, and means for detecting a characteristic of an affinity reaction occurring on or in the vicinity of, or a characteristic of a material disposed on or in the vicinity of, the at least one sensing area of the platform.

26. A platform for use in sample analysis, said platform having one or more sensing areas or regions, each for receiving a capture element or elements which when the platform is irradiated with coherent light can interact to provide an indication of an affinity reaction, wherein each capture element includes two or more types of capture molecule, said platform further comprising an optically transparent substrate having a refractive index ($n_1$), a thin, optically transparent layer, formed on one surface of the substrate, said layer having a refractive index ($n_2$) which is greater than ($n_1$), said platform incorporating therein one or multiple corrugated structures comprising periodic grooves which define the one or multiple sensing areas or regions, said grooves being so profiled, dimensioned and oriented that coherent and linearly polarised light incident on said platform is diffracted into individual beams or diffraction orders which interfere resulting in a substantially total extinction of the transmitted beam and an abnormal high reflection of the incident light thereby generating an enhanced evanescent field at a surface of the one or more sensing areas, the platform further including means for generating a light beam and for directing the beam so that it is incident upon the platform on the side of the substrate that does not have the optically transparent layer disposed thereon at an angle which causes evanescent resonance to occur in at least one sensing area of the platform to thereby create an enhanced resonant field in the at least one sensing area of the platform, and means for detecting a characteristic of an affinity reaction occurring on or in the vicinity of, or a characteristic of a material disposed on or in the vicinity of, the at least one sensing area of the platform.

* * * * *